United States Patent [19]

De Angelis et al.

[11] 3,950,525

[45] Apr. 13, 1976

[54] RELAXATION OF SMOOTH MUSCLE IN A MAMMAL

[75] Inventors: Gerald George De Angelis, Wilton; Hans-Jurgen Ernst Hess, Old Lyme, both of Conn.

[73] Assignee: Pfizer Inc., New York, N.Y.

[22] Filed: Apr. 11, 1975

[21] Appl. No.: 567,356

Related U.S. Application Data

[60] Division of Ser. No. 371,483, June 19, 1973, Pat. No. 3,895,112, which is a division of Ser. No. 182,220, Sept. 20, 1971, Pat. No. 3,859,288, which is a continuation-in-part of Ser. No. 78,216, Oct. 5, 1970, abandoned.

[52] U.S. Cl. .............................................. 424/251
[51] Int. Cl.$^2$.................................... A61K 31/505
[58] Field of Search ................................... 424/251

[56] References Cited
UNITED STATES PATENTS

| | | | |
|---|---|---|---|
| 1,915,334 | 6/1933 | Salzberg et al. ................. | 260/256.4 |
| 3,707,560 | 12/1972 | De Angeles et al. ............ | 260/256.5 |

*Primary Examiner*—Stanley J. Friedman
*Attorney, Agent, or Firm*—Connolly and Hutz

[57] ABSTRACT

4-Amino-6-arylpyrimidines and salts thereof, a novel class of inhibitors of platelet aggregation and bronchodilators in mammals, and 4-hydroxy-6-arylpyrimidines as useful intermediates.

1 Claim, No Drawings

RELAXATION OF SMOOTH MUSCLE IN A MAMMAL

This application is a divisional of application Ser. No. 371,483 filed June 19, 1973, now U.S. Pat. No. 3,895,112, which is a divisional of application Ser. No. 182,220 filed Sept. 20, 1971 now U.S. Pat. 3,859,288 which is a continuation in part of application Ser. No. 78,216 filed Oct. 5, 1970 now abandoned.

BACKGROUND OF THE INVENTION

This invention relates to 6-arylpyrimidines, and more particularly to a series of 4-substituted amino derivatives and salts thereof and to the use of said agents as inhibitors of platelet aggregation and bronchodilators in mammals, and to a series corresponding 4-hydroxy derivatives, useful as intermediates. The invention is further concerned with 4-hydroxy-5-ethyl-6-phenyl-pyrimidine and its use as a bronchodilator.

The synthesis of 4-amino-6-phenylpyrimidine has been reported by Bredereck, et al., Chem. Ber., 90, 942 (1957) and by van der Plas, et al., Tetrahedron Lett., No. 31, 2093 (1964), with no disclosure of utility. The preparation, also without mention of use, of 4-amino-6-(p-t-butylphenyl)pyrimidine was reported by van der Plas, Rec. Trav. Chim., 84, 1101 (1965).

Khromov-Borisov, Dokl. Akad. Nauk. USSR, 180, 1129 (1968) has reported properties of 4-amino-6-methylpyrimidine with no utility disclosure.

SUMMARY OF THE INVENTION

The inhibitors of platelet aggregation of this invention are represented by the formula.

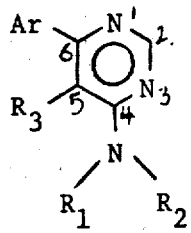

and the acid addition salts thereof, wherein:

Ar is selected from the group consisting of phenyl; monosubstituted phenyl wherein said substituent is methyl, methoxy, 3,4-dimethoxy, hydroxy, trifluoromethyl, fluorine, chlorine, bromine, carboxy, cyano, nitro, dialkylamino said alkyl containing from 1 to 3 carbon atoms, amino or acylamino containing from 1 to 4 carbon atoms; pyridyl; thienyl; furyl; monosubstituted pyridyl, thienyl or furyl wherein said substituent is acylamino containing from 1 to 4 carbon atoms; naphthyl; 3-indolyl; 2- and 3-benzothienyl; and 2- and 3-benzofuryl;

$R_1$ and $R_2$ are each selected from the group consisting of hydrogen; alkyl containing from 1 to 4 carbon atoms; substituted ethyl wherein said substituent is selected from the group consisting of 2-dimethylamino, 2-hydroxy and 2,2,2-trifluoro; alkenyl containing from 3 to 4 carbon atoms; pyridylmethyl; 2-monosubstituted phenyl wherein said substituent is carboxy or sulfamoyl; and cycloalkyl containing from 3 to 7 carbon atoms;

$R_1$ and $R_2$ when taken together with the nitrogen atom to which they are attached form a heterocyclic ring of the formula:

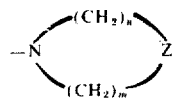

wherein Z is selected from the group consisting of $CH_2$, O, S and N-alkyl containing from 1 to 3 carbon atoms; and $n$ and $m$ are integers of from 2 to 3; and $R_3$ is selected from the group consisting of hydrogen and alkyl containing from 1 to 3 carbon atoms.

Of particular interest, because of their potency for inhibition of platelet aggregation, are compounds wherein $R_1$ and $R_2$ are each hydrogen, alkyl up to 4 carbon atoms and substituted ethyl where acid substituent is 2-hydroxy or 2,2,2-trifluoro, Ar is phenyl or monosubstituted phenyl and $R_3$ is hydrogen or alkyl containing from 1 to 3 carbon atoms.

In addition to their activity as inhibitors of platelet aggregation several compounds of the instant invention are potent relaxants of smooth muscle and in particular bronchial tissue. Of particular interest as bronchodilators are congeners where $R_1$ and $R_2$ are alkyl of up to 4 carbon atoms, Ar is acylamino-substituted phenyl or naphthyl and $R_3$ is hydrogen or alkyl containing from 1 to 3 carbon atoms.

Also part of the present invention are a series of 4-hydroxy-6-arylpyrimidines of the formula:

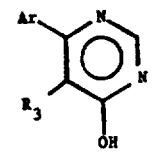

wherein:

$R_3$ is selected from the group consisting of hydrogen and alkyl containing from 1 to 3 carbon atoms; and Ar is selected from the group consisting of phenyl provided that when Ar is phenyl, $R_3$ is ethyl; substituted phenyl wherein said substituent is methyl, methoxy, 3,4-dimethoxy, hydroxy, trifluoromethyl, fluorine, chlorine, bromine, carboxy, cyano, nitro, dialkylamino said alkyl containing from 1 to 3 carbon atoms, amino or acylamino containing from 1 to 4 carbon atoms; pyridyl thienyl; furyl; monosubstituted pyridyl, thienyl or furyl wherein said substituent is acylamino containing from 1 to 4 carbon atoms; naphthyl; 3-indolyl; 2- and 3-benzothienyl; and 2- and 3-benzofuryl.

In addition to their utility as intermediates leading to the corresponding 4-amino-6-arylpyrimidines, one of the above-mentioned 4-hydroxypyrimidines, namely, 4-hydroxy-5-ethyl-6-phenylpyrimidine, possesses unexpected activity as a relaxant of smooth muscle and in particular, bronchial tissue.

DETAILED DESCRIPTION OF THE INVENTION

In accordance with the process employed for the preparation of compounds of the instant invention, several alternate synthetic methods are used. The first synthetic route, Method A, is illustrated by the following scheme:

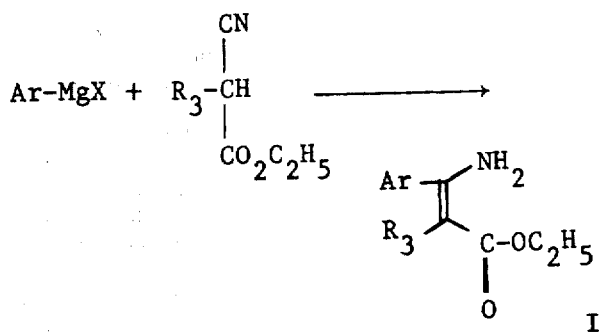

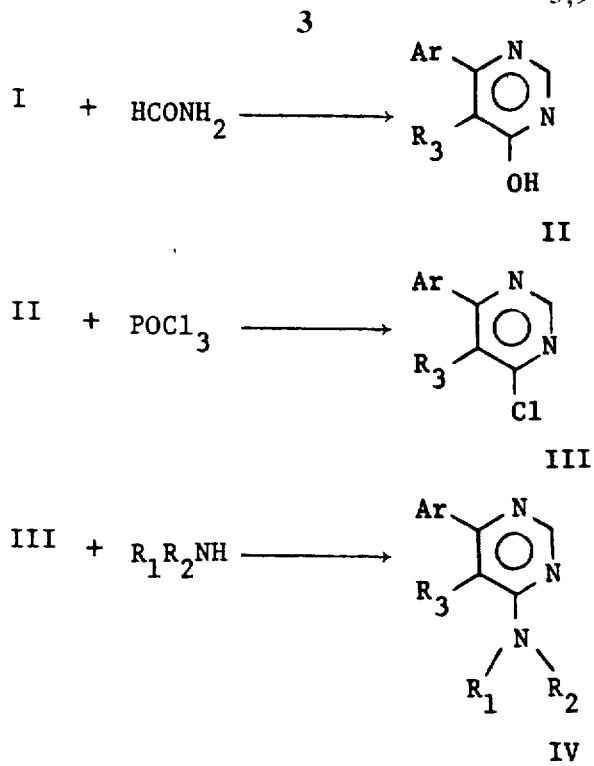

In the first reaction step of the aforementioned scheme, an aryl Grignard is contacted with an ester of cyanoacetate in a reaction inert solvent. In practice, the aryl Grignard, generated in situ from the aryl halide and magnesium turnings in a solvent such as ether, is treated with an ester of cyanoacetate, generally the methyl or ethyl ester, in the same solvent. It is desirable to use at least a 200% excess of the requisite Grignard reagent to effect a maximum yield of product.

The aforedescribed reaction is carried out at ambient temperatures for several hours followed by subsequent hydrolysis of the reaction mixture with dilute sulfuric acid and extraction of the amino ester into the ether phase. Removal of the solvent is followed by purification by distillation if the product (I) is an oil or recrystallization when a solid.

Alternately, an aryl lithium salt can be used in place of the Grignard reagent without markedly affecting the course of the reaction.

The requisite Grignard reagents are available commercially or can be synthesized from the corresponding aryl halide, which are commercial products, by methods available to those skilled in the art, e.g., as outlined by Kharasch, et al., "Grignard Reactions of Nonmetallic Substances," Prentice-Hall, New York, 1954.

Cyclization of the β-amino arylacrylic esters (I) to the 4-hydroxy-6-arylpyrimidines (II) is carried out in a highly polar, reaction-inert solvent such as dimethylsulfoxide or dimethylformamide employing a five to ten fold excess of formamide and at least two equivalents of an alkali metal lower alkoxide such as potassium t-butoxide or sodium ethoxide. Temperatures of from 75°–100° C. are employed with reaction times of 5–24 hours. Isolation of the desired product is carried out by pouring the reaction mixture onto ice followed by acidification with glacial acetic acid. Further purification is effected by recrystallization from a suitable solvent.

The action of halogenating agents such as thionyl chloride, phosphorous oxychloride or phosphorous pentachloride converts the 4-hydroxy-6-arylpyrimidines (II) to the 4-chloro analog (III). Experimentally, II is added to a large excess of the chlorinating reagent, preferably phosphorous oxychloride, and the mixture heated to reflux from 1 to 2 hours. Lower temperatures can be employed with correspondingly longer reaction times. After removal of excess reagent in vacuo, the residual product is poured into a mixture of ammonium hydroxide and ice. The crude product can be used in the next reaction or may be further purified via recrystallization.

Displacement of the 4-chloro substituent of compounds of formula III, leading to the products of the present invention, is carried out in a reaction-inert solvent, e.g., ethanol or tetrahydrofuran with ammonia or an amine, $HNR_1R_2$ wherein $R_1$ and $R_2$ are as previously described. Alternately, the reaction can be carried out neat, i.e., without solvent. In practice, at least 2 moles of ammonia or amino per mole of III is employed, and as much as a 10 fold excess can be employed. It is generally advantageous to heat the aforementioned reaction from about 50°–100° C. for periods of 2–8 hours. Work-up of the reaction constitutes pouring the mixture into water followed by extraction of IV into a non-aqueous solvent such as chloroform and subsequent conversion of the free base to a suitable salt, e.g., hydrochloride, by treating a solution of said base with the appropriate acid.

Also within the scope of this invention are compounds of formula IV wherein a methyl or ethyl substituent exists at the 2-position. Introduction of the methyl or ethyl substituent into the 2-position requires the use of acetamide or propionamide in place of formamide in the second step of the described sequence. In general, the substitution of the aforementioned starting materials does not markedly affect the course or yields of the reactions involved.

Method A is particularly applicable to the preparation of compounds of formula IV wherein $R_1$, $R_2$ and $R_3$ are as previously described and where Ar is pyridyl, thienyl, furyl, naphthyl, 3-indolyl, 2- and 3-benzothienyl, 2- and 3-benzofuryl, phenyl and monosubstituted phenyl where said substituents are methyl, methoxy, 3,4-dimethoxy, trifluoromethyl, fluorine, chlorine and bromine.

Also within the purview of this invention are congeners of IV wherein Ar includes 3,4-methylenedioxyphenyl, acetylphenyl and disubstituted phenyl where the second substituent is selected from the the group consisting of methyl, methoxy, fluorine, chlorine, bromine and ethoxy.

The first alternate series of reactions, Method B, leading to the products of the present invention, is outlined as follows:

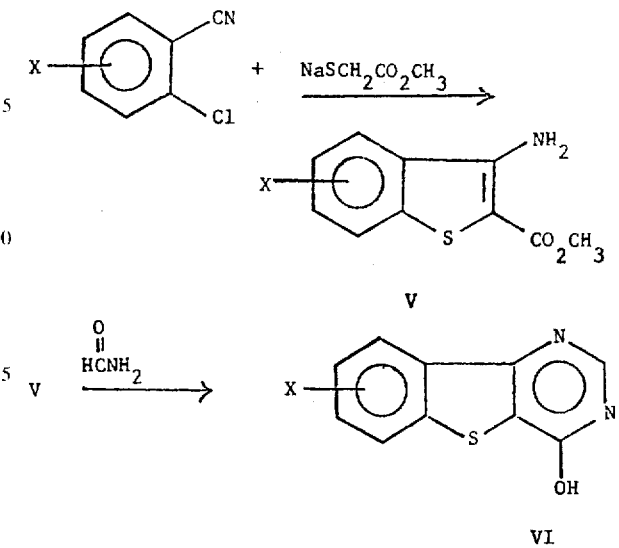

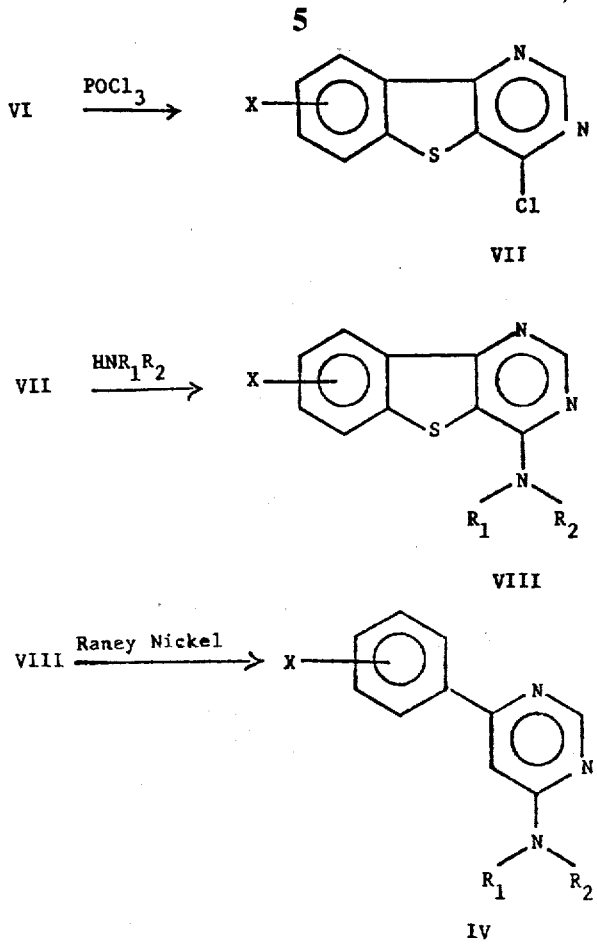

In the first reaction of the aforementioned Method B an appropriately substituted o-chlorobenzonitrile is contacted with a salt of a lower alkyl thioglycolate ester in a reaction-inert solvent. In practice, sodium methyl thioglycolate, prepared by treating methyl thioglycolate with an equivalent amount of sodium alkoxide in a lower alkanol solvent followed by removal of the solvent in vacuo, is added to a reaction-inert solvent, preferably of moderately high polarity, e.g., dimethylformamide or hexamethylphosphoramide. The resulting solution or suspension of sodium methyl thioglycolate is treated with an equimolar amount of the requisite o-chlorobenzonitrile dissolved in the same solvent.

Alternately, the sodium salt of the methyl thioglycolic can be generated in situ in said reaction employing either an equimolar amount of sodium hydride or a sodium alkoxide.

The aforedescribed reaction is carried out at 50°-100° C. for a period of 15 minutes to 2 hours. A convenient method of isolation is to cool the reaction mixture and subsequently add it to a mixture of ice and water. The desired product can be filtered, dried, and recrystallized from a suitable solvent.

The requisite o-chlorobenzonitriles are available commercially or can be synthesized by one skilled in the art, e.g., by the method of Nakaoka, et al., German Pat. No. 1,230,026 (C.A. 66, 55255e).

Cyclization of the 2-carbomethoxy-3-aminobenzothiophenes (V) to the tricyclic 4-hydroxybenzothieno[3,2-d]pyrimidines (VI) is carried out in a reaction-inert solvent such as dimethylsulfoxide or dimethylformamide using a 5 to 10 fold excess of formamide and an equimolar amount of an alkali metal lower alkoxide such as sodium methoxide or potassium t-butoxide. Reaction temperatures of 75°-100° C. are employed with a reaction time of 30 minutes to 2 hours.

The desired product is isolated by pouring the cooled reaction mixture into water followed by acidification with acetic acid, filtration and drying. The product can be further purified by trituration or recrystallization from a suitable solvent.

The action of halogenating agents, e.g., thionyl chloride, phosphorous oxychloride or dichlorophenylphosphine oxide converts the 4-hydroxybenzothieno[3,2-d]pyrimidines (VI) to the corresponding 4-chloro analogs (VII). In practice, VI is added to a large excess of the appropriate reagent, preferably phosphorous oxychloride, and the mixture heated. Reflux temperatures are preferred, although lower temperatures may be employed with correspondingly longer reaction times. The reaction period is not critical, but will vary with temperature, concentration and reactivity of the starting reagents. In general, a period of from about 2 to about 8 hours is operable. A convenient method of isolation comprises removal of the excess phosphorous oxychloride in vacuo followed by treatment of the residue with water and sufficient ammonium hydroxide solution to render the solution basic. The resulting product is filtered and air dried. It can be used in this crude state for subsequent reaction or can be recrystallized from an appropriate solvent.

Displacement of the 4-chloro substituent of compounds of formula VII, leading to VIII, is effected in a reaction-inert solvent with ammonia or an amine, $HNR_1R_2$ wherein $R_1$ and $R_2$ are as previously described. In practice, a mixture of the appropriately substituted 4-chlorobenzothieno[3,2-d]pyrimidine and ammonia or a suitable amine are heated in a solvent such as ethanol, dimethylformamide, benzene or tetrahydrofuran. It is advantageous to employ at least 2 moles of amine per mole of halide, and as much as a 10 fold excess can be employed. It is generally desirable to heat the aforementioned reaction mixture to temperatures from about 40°-150° C., with a preferred range of 75°-100° C. Reaction times are not critical, and will vary with reaction temperature, molar quantities of reactants, etc. In general, periods of 1 to 6 hours are operable.

Isolation of the products following the aforedescribed reaction is most conveniently carried out by diluting with water followed by extraction with a water immiscible solvent, e.g., chloroform, ether or benzene. The separated, non-aqueous phase is then dried over a suitable drying agent and the solvent removed in vacuo.

The final reaction of Method B, leading to the products of the present invention, comprises desulfurization of the 4-aminobenzothieno[3,2-d]pyrimidines (VIII) using an excess of Raney nickel. Experimentally, the reaction is carried out in a highly polar, reaction-inert solvent such as dimethylformamide and at temperatures of 125°-150° C. Reaction times are not critical, but the preferred range is from 24–48 hours. Removal of the spent Raney nickel followed by concentration of the filtrate to dryness provides the crude free base of the desired product, which is converted to hydrochloride salt by conventional methods. Products isolated by Method B prove to be identical with those synthesized by Method A.

The aforedescribed method is particularly useful for the preparation of products of the instant invention wherein $R_1$ and $R_2$ are as previously described, $R_3$ is hydrogen and Ar is phenyl and mono- or disubstituted phenyl where said substituent is methyl, methoxy 3,4-dimethoxy, cyano or carboxy.

The third alternate approach to the synthesis of compounds of the present invention (Method C) is outlined in the following scheme:

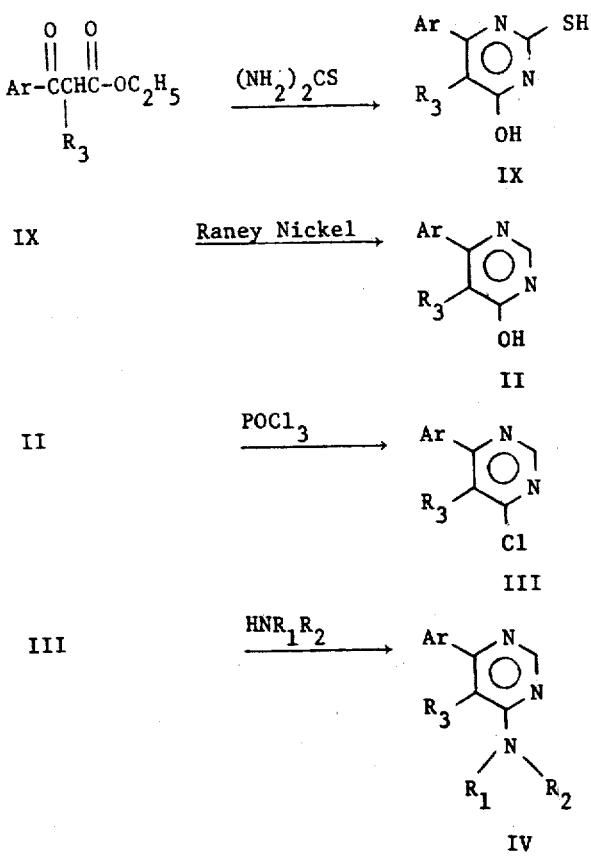

The initial step in the reaction sequence of Method C is a condensation of a (lower)alkyl aroylacetate with thiourea resulting in the formation of a 4-hydroxy-2-mercapto-6-arylpyrimidine (IX). In practice, the requisite β-ketoester is contacted with approximately equimolar amounts of thiourea in a reaction-inert solvent such as those represented by the (lower)alkanols. Temperatures of 60°–90° C. are operable with corresponding reaction times of about 96–140 hours. Isolation of the desired product is achieved by concentration of the reaction mixture in vacuo followed by dilution with water, acidification to pH 3, cooling and, finally, filtration of the crude solids.

Alternately, 5-methylisothiourea may also be employed in place of urea in the above described reaction and provides the corresponding 2-methylthio analog of IX.

The aroylacetates are either commercial products or can be conveniently synthesized by methods available to those skilled in the art, e.g., according to those extensively outlined by Hauser, et al., in "Organic Reactions," John Wiley & Sons, Inc., New York, 1954, Chapter 9, page 266. Aroyl-α-substituted-acetates, ArCOCH($R_3$)$CO_2C_2H_5$, are synthesized according to the procedure as taught by Hope, et al., J. Chem. Soc., 95, 2045 (1909).

Desulfurization of IX in aqueous sodium hydroxide using Raney nickel results in the formation of the corresponding 4-hydroxy-6-arylpyrimidine (II), identical to that prepared by Method A. Similarly, when the corresponding 5-methyl analog of IV is employed, identical products are obtained.

The subsequent steps of the reaction sequence, Method C, and corresponding results are identical to those of Method A.

Method C is especially useful for the preparation of compounds of the instant invention where $R_1$, $R_2$ and $R_3$ are as indicated previously and where Ar is phenyl or mono- or disubstituted phenyl said substituents being cyano, methyl, methoxy, carboxy, acylamino or dialkylamino, pyridyl, furyl and acylamino substituted pyridyl and furyl, 3-indolyl, naphthly and 2- and 3-benzofuryl.

Further, the use of an α-alkylaroylacetate in the initial reaction of Method C allows the synthesis of 5-alkyl congeners of the final products (IV). Substitution of acetamidine or propionamidine for thiourea leads to analogs of IV bearing a 2-methyl or 2-ethyl substituent.

Introduction of a nitro substituent into the aryl moiety of the 4-amino-6-arylpyrimidines can be carried out by direct nitration employing a mixture of nitric and sulfuric acids. In practice, to a solution of the substrate in concentrated sulfuric acid is added, dropwise and at room temperature, nitric acid. The resulting reaction is carried out at ambient temperatures for about 2–6 hours. The reaction is quenched with ice, made basic with ammonium hydroxide and the free base extracted into a water immiscible solvent such as chloroform or methylene chloride.

In general, more than one nitro- isomer is formed as a result of direct nitration. These isomers can subsequently be separated by conventional methods known to those skilled in the art, e.g., by fractional crystallization or column chromatography. Identification of said isomers is most conveniently carried out using nuclear magnetic resonance studies.

Treatment of the aforedescribed nitro compounds with reducing agents, such as stannous chloride and hydrochloric acid, results in the preparation of the corresponding amino analogs. Stannous chloride reductions are carried out at temperatures of 40°–75° C. with reaction times of 2 to 4 hours, and preferably employ 12N hydrochloric acid. The product, which is frequently sparingly soluble as the dihydrochloride salt in 12N hydrochloric acid, is filtered from the cooled reaction mixture and the free base liberated by treatment of the salt with an aqueous base such as sodium hydroxide solution.

In addition to the aforementioned method of reducing nitro substituents, several other reducing reagents, known to those skilled in the art, can be employed with comparable results, e.g., tin-hydrochloric acid, hydrogen-platinum oxide, or aluminum amalgam.

4-Amino-6-aminoarylpyrimidines, resulting from the above-mentioned reduction of the corresponding nitro compounds, can subsequently be reacted with a wide variety of reagents, including alkanoyl halides, anhydrides, alkyl halides, sulfonyl halides, isocyanates and thioisocyanates.

Reaction of said amino compounds with alkanoyl halides and alkoxycarbonyl halides leads to the preparation of the corresponding acylamino and alkyl carbamates, respectively. In practice, the alkanoyl or alkoxycarbonyl halide is added dropwise to a mixture of the appropriate amino compound and an alkali metal carbonate in a suitable reaction-inert solvent such as benzene, ether or methylene chloride. The reaction is preferably carried out at ambient temperatures for a reaction period of about 12 to 24 hours. Hydrolysis of the reaction with water and separation of the water immiscible solvent leads to the subsequent isolation of the crude product.

Analogously, sulfonyl halides are reacted under similar conditions and give rise to the corresponding sulfonamides.

Formation of acylamino substituents employing simple anhydrides or mixed anhydrides in place of aroyl or alkanoyl halides can be carried out with equal ease. Experimentally, the amino compound is contacted with at least an equimolar amount of the requisite anhydride and preferably a 20–50% excess. A solvent, such as benzene, pyridyne, chloroform or tetrahydrofuran, can be employed, or the reaction can be run neat, i.e., without solvent. In the latter case it is desirable to use as much as a 100–300% excess of the appropriate anhydride. Said reaction is carried out for 12 to 24 hours at ambient temperatures. The excess anhydride can be removed under reduced pressure and the residue dissolved in ethyl acetate after which it is convered to the desired salt or alternately, the original reaction mixture can be diluted with ethyl acetate and the salt prepared directly by conventional methods.

Reaction of 4-amino-6-aminoarylpyrimidines with isocyanates and isothiocyanates gives rise to the corresponding ureas and thioureas. Said reactions are effected with the appropriate amino substrate and an equimolar amount, plus as much as a 20% excess, of the requisite isocyanate or thioisocyanate in a reaction-inert solvent, e.g., ether, tetrahydrofuran or benzene. Reaction times of about 12 to 24 hours at room temperature are generally adequate. Isolation of the desired product is achieved by removal of the solvent under reduced pressure followed by recrystallization of the residue from a suitable solvent.

Synthesis of 6-(N-alkylaminoaryl)pyrimidines and 6-(N,N-dialkylaminoaryl)pyrimidines is conveniently carried out by direct alkylation of the 6-aminoaryl-pyrimidines using an appropriate alkyl halide. The extent of alkylation is controlled by the relative amount of alkyl halide, generally the iodide, to the amino compound employed. For mono alkylation equimolar quantities of the two reactants are used plus a small, 10%, excess of the alkyl halide; dialkylation requires at least two moles of halide per mole of amino substrate. Allylic halides and aralkyl halides can also be used with similar ease.

In practice, a solution or suspension of the aminoarylpyrimidine and at least an equimolar amount of an alkali metal carbonate is treated with the appropriate alkyl halide, preferably the iodide, in the amounts previously described. The solvents for this alkylation can vary in nature and are selected from the group including (lower)alkanols, N,N-di(lower)alkyl(lower)alkyl-carboxamides, cyclic ethers and water. Elevated temperatures of from 50°–110° C. are employed, with reaction times of 1–8 hours. The product is isolated by evaporation of the reaction solvent in vacuo followed by extraction of the residue with such solvents as methylene chloride or chloroform or, alternately, when water is used as the reaction solvent the product can be extracted from the mixture directly using said solvents. The separated extracting solvent is evaporated to dryness and the crude product purified by recrystallization from a suitable solvent or chromatographing on a silica gel column.

Also considered within the scope of the present invention are congeners wherein $R_1$ and $R_2$ when considered together with the nitrogen atom to which they are attached form a piperazine ring of the formula

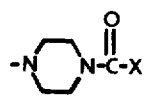

where X is (lower)alkyl, (lower)alkoxy, (lower)alkyleneoxy, phenyl, furyl, thienyl, di(lower)alkylamino, 1-piperidyl and ar(lower)alkyloxy.

As has been previously noted, compounds of the instant invention can form acid addition salts. Basic compounds of the present invention are converted to the acid addition salts by interaction of the base with an acid either in an aqueous or non-aqueous medium. In a similar manner, treatment of the acid addition salts with an aqueous base solution, e.g., alkali metal hydroxides, alkali metal carbonates and alkali metal bicarbonates or with a metal cation which forms an insoluble precipitate with the acid anion, results in a regeneration of the free base form. Such conversions are best carried out as rapidly as possible and under temperature conditons and method dictated by the stability of said basic products. The bases thus regenerated may be reconverted to the same or a different acid addition salt.

In the utilization of the chemotherapeutic activity of those compounds of the present invention which form salts, it is preferred, of course, to use pharmaceutically acceptable salts. Although water-insolubility, high toxicity, or lack of crystalline nature may make some particular salt species unsuitable or less desirable for use as such in a given pharmaceutical application, the water insoluble or toxic salts can be converted to the corresponding pharmaceutically acceptable bases by decomposition of the salt as described above, or alternately they can be converted to any desired pharmaceutically acceptable acid addition salt.

Examples of acids which provide pharmaceutically acceptable anions are hydrochloric, hydrobromic, hydroiodic, nitric, sulfuric, or sulfurous, phosphorous, acetic, lactic, citric, tartaric, succinic, maleic, and gluconic.

The terminal complication of thrombus formation in ischaemic heart disease, cerebral vascular disease, leg-vein thrombosis, pulmonary embolism and peripheral vascular disease is well documented in the medical literature, and has recently been reviewed by Mustard, et al., Pharm. Rev., 22, 97 (1970). The causal role of platelet aggregation in the formation of thrombi, which are masses of agglutinated platelets and leucocytes as distinguished from clots in which the elements of the blood are randomly distributed, has been postulated by many medical studies and has been reviewed by Mustard, et al. The compounds of the instant invention mediate their remarkable antithrombogenic activity through their ability to inhibit the aforementioned platelet aggregation.

As previously indicated, the 4-amino-6-arylpyrimidines of the present invention are all readily adapted to therapeutic use as inhibitors of platelet aggregation. Typical member compounds of interest in this series include 4-diethylamino-6-(p-methoxyphenyl)pyrimidine, 4-diethylamino-6-phenylpyrimidine, 4-(ethyl-n-propylamino)-6-phenylpyrimidine, 4-diethylamino-6-(2-thienyl)pyrimidine, 4-diethylamino-6-(m-dimethylaminophenyl)pyrimidine, 4-[ethyl(2-hydroxyethyl)amino]-6-phenylpyrimidine, 4-ethylamino-6-phenylpyrimidine, 4-(2,2,2-trifluoroethylamino)-6-phenylpyrimidine, 4-diethylamino-5-methyl-6-phenylpyrimidine and 4-diethylamino-5-ehtyl-6-phenylpyrimidine.

In addition to their usefulness as inhibitors of platelet aggregation, several congeners of this series show outstanding potency as smooth muscle relaxants and in particular as bronchodilators. Compounds notable for this therapeutic usefulness include 4-diethylamino-6-(m-acetylaminophenyl)pyrimidine, 4-diethylamino-6-(m-isobutrylaminophenyl)pyrimidine, 4-diethylamino-6-(m-propionylaminophenyl)pyrimidine, 4-di-n-propylamino-6-(m-acetylaminophenyl)-pyrimidine and 4-diethylamino-6-(p-acetylaminophenyl)pyrimidine.

The 4-hydroxy-6-arylpyrimidines of the present invention, as previously mentioned, are useful intermediates leading to the synthesis of the corresponding 4-amino-6-arylpyrimidines. In addition, it has been found that at least one of these intermediates, 4-hydroxy-5-ethyl-6-phenylpyrimidine, has unexpected, outstanding activity as a bronchodilator. It is especially interesting, since the corresponding analogs wherein $R_3$ is hydrogen, methyl propyl have considerably less activity.

The 4-amino-6-arylpyrimidines and 4-hydroxy-5-ethyl-6-phenylpyrimidine and the pharmaceutically acceptable salts thereof, which are useful as inhibitors of platelet aggregation and/or bronchodilators in mammals, may be administered either as individual therapeutic agents or as mixtures of therapeutic agents. They may be administered alone, but are generally administered with a pharmaceutical carrier selected on the basis of the chosen route of administration and standard pharmaceutical practice. For example, they may be combined with various pharmaceutically acceptable inert carriers in the form of tablets, capsules, lozenges, troches, hard candies, powders, sprays, aqueous suspensions or solutions, injectable solutions, elixirs, syrups and the like. Such carriers include solid diluents, or filters, sterile aqueous media and various nontoxic organic solvents. Moreover, the oral pharmaceutical compositions of this invention may be suitably sweetened and flavored by means of various agents of the type commonly used for this purpose.

The particular carrier selected by the proportion of active ingredient to the carrier are influenced by the solubility and chemical nature of the therapeutic compounds, the chosen route of administration and the needs of the standard pharmaceutical practice. For example, where those compounds are administered orally in tablet form, excipients such as lactose, sodium citrate, calcium carbonate and dicalcium phosphate may be used. Various disintegrants such as starch, alginic acids, and certain complex silicates together with lubricating agents such as magnesium stearate, sodium lauryl sulphate and talc, may also be used in producing tablets for the oral administration of these compounds. For oral administration in capsule form, lactose and high molecular weight polyethylene glycols are among the preferred materials for use as pharmaceutically acceptable carriers. Where aqueous suspensions are to be used for oral administration, the compounds of this invention may be combined with emulsifying or suspending agents. Diluents such as ethanol, propylene glycol, glycerine and their combinations may be employed as well as other materials.

For purposes of parenteral administration and inhalation, solutions or suspensions of the instant compounds in sesame or peanut oil or in aqueous propylene glycol solutions can be employed, as well as sterile aqueous solutions of the soluble acid addition salts described hereinafter. These particular solutions are especially suited for intramuscular and subcutaneous injection purposes. The aqueous solutions, including those of the acid addition salts dissolved in pure distilled water, are also useful for intravenous injection purposes provided that their pH is properly adjusted beforehand. Such solutions should also be suitably buffered, if necessary, and the liquid diluent first rendered isotonic with sufficient saline or glucose.

The compounds may be administered to subjects suffering from bronchoconstriction by means of inhalators or other devices which permit the active compounds to come into direct contact with the constricted areas of the tissues of the subject. When administered by means of a spray formulated as a 1% solution, utilization several times a day is preferred.

It is necessary that the active ingredient form a proportion of the composition such that a suitable dosage form will be obtained. Obviously, several dosage unit forms may be administered at about the same time. Although compositions with less than 0.005% by weight of active ingredient might be used in certain instances, it is preferred to use compositions containing not less than 0.005% of the active ingredient; otherwise the amount of carrier becomes excessively large. Activity increases with the concentration of the active ingredient. The composition may contain 10, 50, 75, 95 or an even higher percentage by weight of the active ingredient.

Although the use of the present invention is directed toward the treatment of mammals in general, the preferred subject is human. In determining an efficacious dose for human therapy, results of animal testing are frequently extrapolated and a correlation is assumed between animal test behavior and proposed human dosage. When a commercially employed standard is available, the dose level of the clinical candidate in humans is frequently determined by comparison of its performance with the standard in an animal test. For example, theophylline is employed as a standard bronchodilator and is administered to humans at the rate of 150 to 300 mg. every 4 hours. It is assumed, then, that if compounds of the present invention have acitvity comparable to theophylline in the test assay, that similar doses will provide comparable responses in humans.

Obviously, the physician will ultimately determine the dosage which will be most suitable for a particular individual, and it will vary with the age, weight and response of the particular patient as well as with the nature and extent of the symptoms and the pharmacodynamic characteristics of the particular agent to be administered. Generally, small doses will be administered initially, with a gradual increase in the dosage until the optimum level is determined. It will often be found that when the composition is administered orally, larger quantities of the active ingredient will be required to produce the same level as produced by a small quantity administered parenterally.

Having full regard for the foregoing factors it is considered that an effective daily dosage of the compounds of the present invention in humans of approximately 50–750 mg. per day, with a preferred range of about 50–350 mg. per day in single or divided doses, or at about 1 to 7 mg./kg. of body weight will effectively prevent thrombus formation in human subjects prone to said disorder, and alleviate bronchoconstriction. These values are illustrative, and there may, of course, be individual cases where higher or lower dose ranges are merited.

The following examples are provided 3,2for the purpose of illustration and are not to be construed as limitations of this invention, many variations of which are possible without departing from the spirit or scope thereof.

EXAMPLE I

4-Diethylamino-6-phenylpyrimidine hydrochloride

Method A.

A. Ethyl 2-aminocinnamate (I; Ar = $C_6H_5$)

To a solution of dry ethyl ether (300 ml.) is added magnesium turnings (16.9 g.). Bromobenzene (103 g.) in ether (600 ml.) is added at a rate to maintain gentle refluxing (An iodine crystal or a ml. of methyliodide often must be added to initiate the reaction.). Refluxing is continued until most of the magnesium has reacted. Ethyl cyanoacetate (30 g.) is added over a 30 minute period and the reaction mixture allowed to stir for 3 hours at room temperature after which time 3.5N sulfuric acid (180 ml.) is added and the reaction allowed to stir for 30 additional minutes. The aqueous layer is extracted with diethyl ether and the organic layer washed with water and dried over sodium sulfate. Removal of the ether in vacuo followed by distillation of the residual oil gives the desired product, b.p. at 0.4 mm, 138°–142° C.

B. 4-Hydroxy-6-phenylpyrimidine (II; Ar = $C_6H_5$; $R_3$ = H)

To a mixture of ethyl 2-aminocinnamate (54 g.; 0.28 mole) and formamide (100 ml.) in dimethylsulfoxide (700 ml.) at 100° C. is added via a dropping funnel potassium t-butoxide (63 g.; 0.56 mole) in 300 ml. of the same solvent over a 15 minute period. The solution is stirred for 16 hours at 100° C. after which time it is cooled, poured over ice (2 l.) and acetic acid added to complete precipitation. The solid obtained upon filtration is washed with water, isopropyl alcohol and air dried, 30 g., m.p. 266°–267° C.

C. 4-Chloro-6-phenylpyrimidine (III; Ar = $C_6H_5$; $R_3$ = H)

4-Hydroxy-6-phenylpyrimidine (2.1 g.) is added to phosphorous oxychloride (60 ml.) and refluxed for 1.5 hours. Excess phosphorous oxychloride is removed in vacuo, and the dark oil poured over concentrated ammonium hydroxide/ice. The precipitate which forms is filtered, washed with water and dried, 2.1 g., m.p. 95°–98° C.

D. 4-Diethylamino-6-phenylpyrimidine hydrochloride (IV; Ar = $C_6H_5$; $R_1$, $R_2$ = $C_2H_5$; $R_3$ = H)

A mixture of 4-chloro-6-phenylpryimidine (10.0 g.), diethylamine (7.5 g.) and ethanol (200 ml.) is refluxed for 5 hours. At the end of this time the reaction mixture is poured into water (800 ml.) and extracted with chloroform. The chloroform layer is dried and concentrated in vacuo to an oil which is taken up in methanol, treated with activated charcoal, filtered and the methanol removed in vacuo. The residual oil is taken up in diethyl ether and anhydrous hydrogen chloride bubbled into the solution until precipitation is complete. Filtration yields the hydrochloride salt (6.45 g.) which is recrystallized from ethanol/hexane to yield a tan microcrystalline solid, 5.0 g., m.p. 214°–215° C.

Anal. Calcd. for $C_{14}H_{17}N_3 \cdot HCl$: C, 63.7; H, 6.9; N, 15.9. Found: C, 63.6; H, 7.0; N, 15.7.

EXAMPLE II

4-Diethylamino-6-phenylpyrimidine hydrochloride

Method B.

A. 2-Carbomethoxy-3-aminobenzothiophene (V; X = H)

To a solution of t-butyl alcohol (30 ml.) and potassium t-butoxide (1.12 g.; 0.01 mole) is added via a dropping funnel methyl thioglycolate (1.06 g.; 0.01 mole) in t-butyl alcohol (10 ml.). The solution is stirred for 10 minutes and then concentrated in vacuo to yield the sodium salt of methyl thioglycolate, which is taken up in 30 ml. of dimethylformamide. To this is added via a dropping funnel 2-chlorobenzonitrile (1.37 g.; 0.01 mole) in dimethylformamide (10 ml.), and the solution is warmed to 75° C. for 30 minutes. At the end of this time the solution is cooled and poured onto 200 ml. of ice and water. The resultant precipitate is filtered, washed with water and dried to yield a white microcrystalline solid, 1.8 g., m.p. 105°–106° C.

B. 4-Hydroxybenzothieno[3,2-d]pyrimidine (VI; X = H)

To a solution of 2-carbomethoxy-3-aminobenzothiophene (2.07 g.; 0.02 mole) and potassium t-butoxide (2.24 g.; 0.02 mole) in dimethylsulfoxide (30 ml.) is added an excess of formamide (ca 5 ml./g. of 2-carbomethoxy-3-aminobenzothiophene). This is heated to 90° C. until the reaction is complete as evidenced by thin layer chromatography (~30 minutes). The solution is cooled, poured into water, acidified with glacial acetic acid and the resultant solid is filtered. Washing with isopropyl alcohol and then ether yields a white solid, 1.76 g., m.p. 300°–301° C.

C. 4-Chlorobenzothieno[3,4-d]pyrimidine (VII; X = H)

A mixture of 4-hydroxybenzothieno[3,2-d]pyrimidine (20 g.; 0.1 mole) in phosphorus oxychloride (500 ml.) is refluxed with stirring for 4 hours. At the end of this time the solution is cooled and concentrated in vacuo to a brown semisolid, which is poured into 250 g. ice/250 ml. ammonium hydroxide solution. The resultant solid is filtered and air dried to yield a beige microcrystalline solid, 19.7 g., m.p. 139°–140° C.

D. 4-Diethylaminobenzothieno[3,2-d]pyrimidine hydrochloride (VIII; X = $R_1$, $R_2$ = $C_2H_5$)

A mixture of 4-chlorobenzothieno[3,2-d]pyrimidine (15 g; 0.068 mole) and an excess of diethylamine in ethanol (500 ml.) is refluxed with stirring for 3 hours. The solution is cooled, poured into water (500 ml.) and extracted with chloroform. The chloroform extracts are washed with water, dried over sodium sulfate and the chloroform removed in vacuo to yield a dark oily residue. This is taken up in methanol, treated with activated charcoal, filtered, and the solent removed in vacuo to yield an oily residue which is taken up in diethyl ether. Anhydrous hydrogen chloride gas is bubbled into this solution unti precipitation ceases. Filtration yields the hydrochloride salt, 13.4 g., m.p. 226°–230° C.

E. 4-Diethylamino-6-phenylpyrimidine hydrochloride (IV; X = H; $R_1$, $R_2$ = $C_2H_5$)

To a solution of 1.5 ml. of dimethylformamide containing 4-diethylaminobenzothieno[3,2-d]pyrimidine (2.0 g.) is added a large excess of Raney nickel and the resulting mixture heated to reflux. Water is allowed to distill from the reaction mixture until the temperature reaches 150° C. where refluxing is continued with rapid stirring for 48 hours. The solids are filtered and the filtrate concentrated in vacuo to an oil. The residual oil is partitioned between water and chloroform and the organic layer separated and dried over sodium sulfate. Removal of the solvent under reduced pressure provides an oil which when dissolved in ethyl ether and treated with gaseous hydrogen chloride provides 1.4 g.

of the hydrochloride salt of the desired product, which is identical in every respect to that synthesized via Method A.

EXAMPLE III

4-Diethylamino-5-ethyl-6-phenylpyrimidine Hydrochloride

Method C.

A. 2-Mercapto-4-hydroxy-6-phenylpyrimidine (V; Ar = $C_6H_5$; $R_3$ = $C_2H_5$)

A reaction vessel is charged with 750 ml. of dry ethanol, 80 g. (0.36 mole) of ethyl α-benzoylbutyrate, 39.3 g. (0.72 mole) of sodium methoxide and 49.3 g. (0.82 mole) of thiourea. The reaction mixture is heated to the reflux temperature (79° C.) and stirred at that point for 120 hours. The resulting reaction mixture is concentrated in vacuo to a low volume and the thick slurry then diluted with 400 ml. of water and ice. The aqueous solution is chilled to 10° C. and then acidified to pH 3.0 by the slow addition of concentrated hydrochloric acid. The crystalline is granulated for 30 minutes at 20° C. and then filtered. The cake is washed with warm water (60 l. at 35° C.) and then dried, 35.8 g., m.p. 233°–236° C.

B. 4-Hydroxy-5-ethyl-6-phenylpyrimidine (II; Ar = $C_6H_5$; $R_3$ = $C_2H_5$)

To a solution of 283 ml. of water containing 11.4 g. of sodium hydroxide and 35 g. of 2-mercapto-4-hydroxy-5-ethyl-6-phenylpyrimidine, under a nitrogen atmosphere and heated to 65° C. is added 265 g. of Raney Nickel in small portions. After heating for 2 hours on a steam bath, an additional 80 g. of Raney Nickel is added. After an hour the desulfurization is complete and the reaction mixture is cooled. The Raney Nickel is filtered, the filtrate is concentrated in volume in vacuo and diluted with ice and water. The aqueous solution is acidified to pH 5.0 with concentrated hydrochloric acid and stirred for 15 minutes. The resulting precipitate is filtered and dried, 22.1 g.; m.p. 180°–182° C. The analytical sample is recrystallized from chloroform-hexane.

Anal. Calcd. for $C_{12}H_{12}N_2O$: C, 72.0; H, 6.0; N, 14.0.
Found: C, 71.9; H, 6.0; N, 14.0.

C. 4-Chloro-5-ethyl-6-phenylpyrimidine (III; Ar = $C_6H_5$; $R_3$ = $C_2H_5$)

A slurry of 21.0 g. of 4-hydroxy-5-ethyl-6-phenylpyrimidine in 250 ml. of phosphorus oxychloride is stirred and heated to the reflux temperature (105°–110° C.). At 78° C. all of the solid materials are dissolved, and the solution then is stirred at 110° C. for 24 hours. The solution is concentrated in vacuo to a volume, and then carefully added at 50° C. to a mixture of concentrated ammonium hydroxide and ice. The precipitate is filtered and the off-white solid is air dried, 21.5 g., m.p. 46°–47° C.

Anal. Calcd. for $C_{12}H_{11}ClN_2$: C, 65.9; H, 5.1; N, 12.8.
Found: C, 65.2; H, 4.9; N, 12.6.

D. 4-Diethylamino-5-ethyl-6-phenylpyrimidine hydrochloride (IV; Ar = $C_6H_5$; $R_3$ = $C_2H_5$)

An ethanol solution of 12 g. of 4-chloro-5-ethyl-6-phenylpyrimidine and 16.1 g. of diethylamine is stirred at the reflux temperature overnight. The ethanol and excess amine are removed in vacuo to provide the residual product as a thick oil. The oil is dissolved in chloroform which is subsequently washed twice with water, dried over sodium sulfate and decolorized with charcoal. The chloroform is removed under reduced pressure, the residual oil taken up in ethyl acetate and dry hydrogen chloride gas added until the precipitate ceases to form. The product is filtered and dried, 6.9 g., m.p. 138°–139.5° C.

The analytical sample was prepared by recrystallisation.

Anal. Calcd. for $C_{16}H_{22}ClN_3$: C, 65.9; H, 7.6; N, 14.4.
Found: C, 66.1; H, 7.6; N, 14.4.

EXAMPLE IV

The procedures of Example I are repeated, using the appropriately substituted starting materials, to provide the following compounds in good yields:

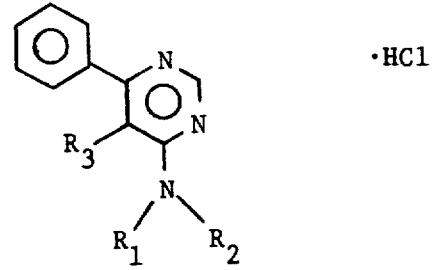

| $R_1$ | $R_2$ | $R_3$ | m.p., C.° | Procedure |
|---|---|---|---|---|
| H | $CH_3$ | H | 218–220 | Example I |
| H | $C_2H_5$ | H | 190–192 | Example I |
| H | n-$C_3H_7$ | H | 172–174 | Example I |
| H | i-$C_3H_7$ | H | 165–167 | Example I |
| H | n-$C_4H_9$ | H | 142–145 | Example I |
| H | i-$C_4H_9$ | H | 138–140 | Example I |
| H | H | H | 207–209 | Example I |
| $CH_3$ | $CH_3$ | H | 250–252 | Example I |
| $CH_3$ | n-$C_3H_7$ | H | 172–174 | Example I |
| $C_2H_5$ | $C_2H_5$ | H | 173–175 | Example I |
| $C_2H_5$ | n-$C_3H_7$ | H | 187–188 | Example I |
| n-$C_3H_7$ | n-$C_3H_7$ | H | 152–154 | Example I |
| n-$C_4H_9$ | n-$C_4H_9$ | H | 90–91 | Example I |
| i-$C_4H_9$ | i-$C_4H_9$ | H | 103–104 | Example I |
| $C_2H_5$ | $C_2H_5$ | $CH_3$ | 201–202.5 | Example III |
| i-$C_3H_7$ | t-$C_3H_7$ | $CH_3$ | 210–212 | Example III |
| $CH_3$ | $CH_3$ | $C_2H_5$ | 163–166 | Example III |
| i-$C_3H_7$ | i-$C_3H_7$ | $C_2H_5$ | 75–78 | Example III |
| $CH_3$ | $CH_3$ | n-$C_3H_7$ | 165–166 | Example III |
| $C_2H_5$ | $C_2H_5$ | n-$C_3H_7$ | 132–134 | Example III |
| $C_2H_5$ | $C_2H_5$ | i-$C_3H_7$ | 95–97.5 | Example III |

EXAMPLE V

Following the procedures of Example II, and starting with the requisite benzothieno[3,2-d]pyrimidine the following products are prepared in moderately good yields:

4-(1-Pyrrolidinyl)-6-phenylpyrimidine hydrochloride, m.p. 266°–268° C.;

4-(1-Piperidyl)-6-phenylpyrimidine hydrochloride, m.p. 278°–280° C.;

4-(1-Hexahydroazepinyl)-6-phenylpyrimidine hydrochloride, m.p. 65° C.;

4-(4-Morpholinyl)-6-phenylpyrimidine hydrochloride, m.p. 259°–260° C.;

4-(4-Methyl-1-piperazinyl)-6-phenylpyrimidine dihydrochloride, m.p. 290°–292° C. (decomposition).

EXAMPLE VI

Again, employing the procedures of Example I, and utilizing the appropriate starting reagents, the following congeners are prepared:

4-(2,2,2-Trifluoroethylamino)-6-phenylpyrimidine hydrochloride, m.p. 195°–197° C.;

4-[Ethyl(2,2,2-trifluoroethyl)amino]-6-phenylpyrimidine hydrochloride, m.p. 208°–210° C.;

4-[2-(Diethylamino)ethylamino]-6-phenylpyrimidine hydrochloride, m.p. 80°–82° C.;

4-[Methyl(2-hydroxyethyl)amino]-6-phenylpyrimidine hydrochloride, m.p. 204°–205° C.;

4-[Ethyl(2-hydroxyethyl)amino]-6-phenylpyrimidine hydrochloride, m.p. 182°–184° C.;

4-[Bis(2-hydroxyethyl)amino]-6-phenylpyrimidine hydrochloride, m.p. 152°–155° C.;

4-(Diallylamino)-6-phenylpyrimidine hydrochloride, m.p., 273°–275° C.;

4-(3-Pyridylmethylamino)-6-phenylpyrimidine dihydrochloride, m.p. 225°–226° C.;

4-[Methyl(3-pyridylmethyl)amino]-6-phenylpyrimidine dihydrochloride, m.p. 262°–266° C.;

Ethyl N-(6-phenyl-4-pyrimidinyl)anthranilate hydrochloride, m.p. 165°–170° C.;

4-Diethylamino-5-ethyl-6-(2-naphthyl)pyrimidine hydrochloride, m.p. 161°–162° C.;

4-Diethylamino-5-ethyl-6-(4-tolyl)pyrimidine hydrochloride, m.p. 103°–104° C.

EXAMPLE VII

Utilizing the amination procedure of Example I-D or III-D, and employing the appropriate 4-chloro-6-phenypyrimidine and the requisite amine, the following congeners are synthesized:

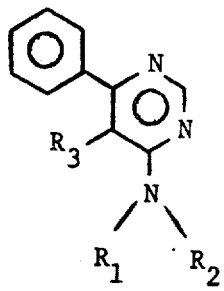

| $R_1$ | $R_2$ | $R_3$ | $R_1$ | $R_2$ | $R_3$ |
|---|---|---|---|---|---|
| cyclo $C_3H_5$ | H— | H | cyclo $C_3H_5$ | $HO(CH_2)_2$— | n-$C_3H_7$ |
| cyclo $C_3H_5$ | $CH_3$— | H | cyclo $C_7H_{13}$ | $HO(CH_2)_2$— | H |
| cyclo $C_3H_5$ | $CH_3$— | $CH_3$ | cyclo $C_7H_{13}$ | $HO(CH_2)_2$— | $C_2H_5$ |
| cyclo $C_3H_9$ | $C_2H_5$— | H | cyclo $C_6H_{11}$ | $(CH_3)_2N(CH_2)_2$— | H |
| cyclo $C_3H_9$ | i-$C_3H_7$— | H | cyclo $C_7H_{13}$ | $(CH_3)_2N(CH_2)_2$— | H |
| cyclo $C_6H_{11}$ | H— | H | cyclo $C_6H_{11}$ | $CH_2=CHCH_2$— | H |
| cyclo $C_6H_{11}$ | $CH_3$— | H | cyclo $C_6H_{11}$ | $CH_2=CHCH_2$— | $CH_3$ |
| cyclo $C_6H_{11}$ | $CH_3$ | $C_2H_5$ | cyclo $C_6H_{11}$ | $CH_2=CCH_2$—$\\$ $CH_3$ | |
| cyclo $C_3H_9$ | $CF_3CH_2$— | H | | | |
| cyclo $C_7H_{13}$ | $CF_3CH_2$— | H | | | |
| cyclo $C_3H_5$ | $HO(CH_2)_2$— | H | | | |

| $R_1$ | $R_2$ |
|---|---|
| H | 2-pyridylmethyl |
| $CH_3$ | 2-pyridylmethyl |
| n-$C_3H_7$ | 2-pyridylmethyl |
| H | 3-pyridylmethyl |
| $CH_3$ | 3-pyridylmethyl |
| $CH_3$ | 4-pyridylmethyl |
| H | 2-sulfamoylphenyl |
| $CH_3$ | 2-sulfamoylphenyl |
| n-$C_3H_9$ | 2-sulfamoylphenyl |
| H | 2-carboxyphenyl |
| $CH_3$ | 2-carboxyphenyl |
| i-$C_3H_7$ | 2-carboxyphenyl |

EXAMPLE IX

Following the procedures of Example I, and starting with the appropriate reagents, the following compounds are synthesized:

4-Diethylamino-6-(m-chlorophenyl)pyrimidine hydrochloride, m.p. 178°–180° C.;

4-Diethylamino-6-(p-chlorophenyl)pyrimidine hydrochloride, m.p. 215°–216° C.;

4-Di(n-propyl)amino-6-(p-chlorophenyl)pyrimidine hydrochloride, m.p. 157°–158° C.;

4-Dimethylamino-6-(p-chlorophenyl)pyrimidine hydrochloride, m.p. 268°–270° C.;

4-(1-Pyrrolidinyl)-6-(p-chlorophenyl)pyrimidine hydrochloride, m.p. 265°–267° C.;

4-(4-Methyl-1-piperazinyl)-6-(p-chlorophenyl)pyrimidine hydrochloride, m.p. 295° C.;

4-[Methyl(2-hydroxyethyl)amino]-6-(p-chlorophenyl)pyrimidine hydrochloride, m.p. 203°–205° C.;

4-(2,2,2-Trifluoroethylamino)-6-(p-chlorophenyl)pyrimidine hydrochloride, m.p. 227°–229° C.;

4-Di(n-propyl)amino-6-(m-trifluoromethylphenyl)pyrimidine hydrochloride, m.p. 276°–278° C.

EXAMPLE VIII

The procedures of Example II are repeated, starting with the appropriately substituted benzothieno[3,2-d]pyrimidine, to provide the following analogs:

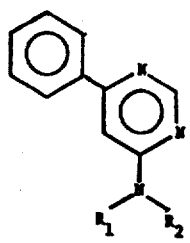

EXAMPLE X

Again, following the procedures of Example I, and starting with the appropriately substituted reagents, the following analogs are prepared in moderate yields:

| X | $R_1$ | $R_2$ | $R_3$ |
|---|---|---|---|
| 2-Cl | H | $CH_3$— | H |

-continued

| X | R₁ | R₂ | R₃ |
|---|----|----|-----|
| 2-Cl | H | CH₃— | CH₃ |
| 2-Cl | —(CH₂)₄— | | H |
| 2-Cl | —(CH₂)₅— | | C₂H₅ |
| 2-Br | CH₃ | CH₃— | H |
| 2-Br | CH₃ | CH₃— | C₂H₅ |
| 2-Br | —(CH₂)₂O(CH₂)₂— | | CH₃ |
| 3-Br | —(CH₂)₂O(CH₂)₂— | | n-C₃H₇ |
| 3-Br | C₂H₅ | n-C₃H₇— | H |
| 3-Br | —(CH₂)₂N(CH₃)(CH₂)₂— | | CH₃ |
| 4-Br | —(CH₂)₂O(CH₂)₂— | | C₂H₅ |
| 4-Br | C₂H₅ | HO(CH₂)₂— | H |
| 4-Br | H | CF₃CH₂— | H |
| 2-I | H | CF₃CH₂— | C₂H₅ |
| 2-F | CH₃ | cyclo C₅H₁₁— | H |
| 2-F | CH₃ | CH₂=CHCH₂— | C₂H₅ |
| 3-F | CH₃ | CH₃ | CH₃ |
| 4-F | CH₂=CHCH₂ | CH₂=CHCH₂— | H |
| 4-F | | —(CH₂)₆— | H |
| 4-F | C₂H₅ | HO(CH₂)₂— | H |
| 4-CF₃ | CH₃ | CH₃— | H |
| 4-CF₃ | CF₃CH₂ | H— | CH₃ |
| 4-CF₃ | C₂H₅ | HO(CH₂)₂— | i-C₃H₇ |
| 4-CF₃ | H | cyclo C₅H₉— | H |

EXAMPLE XI

Repeating again the procedure of Example I or III, and employing the proper starting reagents, the following 6-(p-methoxyphenyl)pyrimidine hydrochlorides are synthesized:

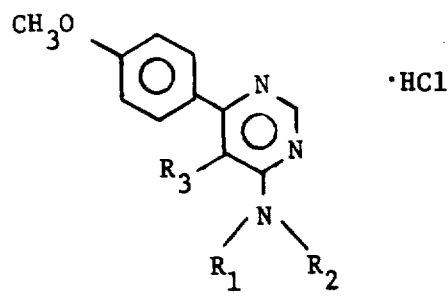

| R₁ | R₂ | R₃ | m.p., °C. |
|----|----|----|-----------|
| H | CH₃ | H | 200–201 |
| H | C₂H₅ | H | 238–240 |
| H | i-C₄H₉ | H | 159–161 |
| H | H | H | 205–207 |
| CH₃ | CH₃ | H | 259–261(decomposition) |
| C₂H₅ | C₂H₅ | H | 222 |
| n-C₃H₇ | n-C₃H₇ | H | 210–211 |
| CH₂=CHCH₂ | CH₂=CHCH₂ | H | 157–159 |
| —(CH₂)₂N(CH₃)(CH₂)₂— | | H | *285–287(decomposition) |
| —(CH₂)₄— | | | 245–247 |
| C₂H₅ | HO(CH₂)₂— | H | 219–221 |
| C₂H₅ | C₂H₅ | C₂H₅ | 129–132 |

*dihydrochloride

In a similar manner are prepared 4-diethylamino-6-(3,4-dimethoxyphenyl)pyrimidine hydrochloride, m.p. 199.5°–201° C., and 4-diethylamino-6-(3-ethoxy-4-methoxyphenyl)pyrimidine, m.p. 218°–219° C.

EXAMPLE XII

Following the experimental details of Example I or III, and starting with the appropriately substituted reagents, the following compounds are prepared:

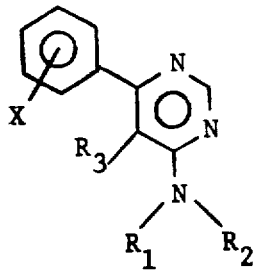

| X | R₁ | R₂ | R₃ |
|---|----|----|-----|
| 2-OCH₃ | H | CH₃ | H |
| 2-OCH₃ | CH₃ | CH₃ | H |
| 2-OCH₃ | CH₃ | CH₃ | CH₃ |
| 2-OCH₃ | n-C₃H₉ | CH₃ | C₂H₅ |
| 2-OCH₃ | n-C₃H₉ | CH₃ | H |
| 2-OCH₃ | —(CH₂)₆— | | H |
| 3-OCH₃ | C₂H₅ | C₂H₅ | H |
| 3-OCH₃ | CH₃ | CH₂=CHCH₂ | H |
| 3-OCH₃ | CH₃ | cyclo C₆H₁₁ | H |
| 3-OCH₃ | CH₃ | (CH₃)₂N(CH₂)₂— | H |
| 4-OCH₃ | H | 4-C₄H₉ | H |
| 4-OCH₃ | CH₃ | CF₃CH₂ | CH₃ |
| 4-OCH₃ | CH₃ | CF₃CH₂ | H |
| 4-OCH₃ | H | CF₃CH₂ | H |
| 4-OCH₃ | | —(CH₂)₂N(i-C₃H₇)(CH₂)₂— | H |
| 4-OCH₃ | | —(CH₂)₂N(i-C₃H₇)(CH₂)₂— | n-C₃H₇ |
| 2-CH₃ | H | cyclo C₇H₁₃ | CH₃ |
| 2-CH₃ | H | cyclo C₇H₁₃ | H |
| 2-CH₃ | CH₃ | cyclo C₃H₅ | H |
| 2-CH₃ | H | CF₃CH₂ | H |
| 2-CH₃ | CF₃CH₂ | CF₃CH₂ | C₂H₅ |
| 2-CH₃ | CF₃CH₂ | CF₃CH₂ | H |
| 3-CH₃ | H | CF₃CH₂ | n-C₃H₇ |
| 3-CH₃ | H | CF₃CH₂ | H |
| 3-CH₃ | | —(CH₂)₂S(CH₂)₂— | H |
| 3-CH₃ | | —(CH₂)₂O(CH₂)₂— | CH₃ |
| 4-CH₃ | H | CH₂=CHCH₂ | H |
| 4-CH₃ | CH₃ | HO(CH₂)₂— | H |
| 4-CH₃ | C₂H₅ | n-C₃H₇ | H |
| 4-CH₃ | H | 2-H₂NSO₂C₆H₄ | C₂H₅ |
| 4-CH₃ | H | 2-H₂NSO₂C₆H₄ | H |
| 4-CH₃ | H | 2-HO₂CC₆H₄ | CH₃ |
| 4-CH₃ | H | 2-HO₂CC₆H₄ | H |

EXAMPLE XIII

4-Diethylamino-6-(p-hydroxyphenyl)pyrimidine hydrobromide

A solution of 18.6 g. (0.1 mole) of 4-diethylamino-6-(p-methoxyphenyl)pyrimidine in 30 ml. of 48% hydrobromic acid and 30 ml. of glacial acetic acid is heated to the reflux temperature and gaseous hydrogen bromide slowly introduced below the surface during the first two hours of refluxing. Heating is continued until thin layer chromatography indicates the reaction is complete. The reaction is cooled and the excess acetic acid and hydrobromic acid are removed under reduced pressure. The residual product is triturated with acetone, filtered and recrystallized from ethanol/hexane.

EXAMPLE XIV

Following the procedure of Example XIII and starting with the 6-(methoxyphenyl)pyrimidines of Example XII and the appropriate reagents the following analogs are prepared:

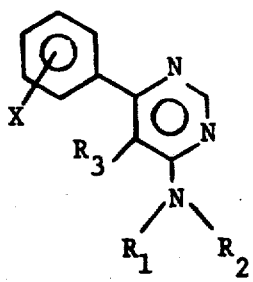

| X | R₁ | R₂ | R₃ |
|---|----|----|----|
| 2-OH | H | CH₃ | H |
| 2-OH | CH₃ | CH₃ | H |
| 2-OH | CH₃ | CH₃ | CH₃ |
| 2-OH | n-C₄H₉ | CH₃ | C₂H₅ |
| 2-OH | n-C₄H₉ | CH₃ | H |
| 2-OH | —(CH₂)₆— | | H |
| 3-OH | C₂H₅ | C₂H₅ | H |
| 3-OH | CH₃ | CH₂=CHCH₂ | H |
| 3-OH | CH₃ | cyclo C₆H₁₁ | H |
| 3-OH | CH₃ | (CH₃)₂N(CH₂)₂— | H |
| 4-OH | H | n-C₄H₉ | H |
| 4-OH | CH₃ | CF₃CH₂ | CH₃ |
| 4-OH | CH₃ | CF₃CH₂ | H |
| 4-OH | H | CF₃CH₂ | H |
| 4-OH | —(CH₂)₂N(i-C₃H₇)(CH₂)₂— | | H |
| 4-OH | —(CH₂)₂N(i-C₃H₇)(CH₂)₂— | | n-C₃H₇ |

EXAMPLE XV

The method of Example III is repeated, using the requisite starting reagents, to provide the following congeners in moderate yields:

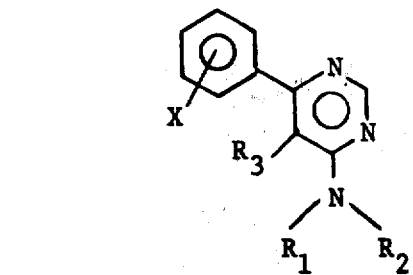

| X | R₁ | R₂ | R₃ |
|---|----|----|----|
| 2-CO₂H | CH₃ | H | H |
| 2-CO₂H | CH₃ | CH₃ | H |
| 2-CO₂H | CH₃ | i-C₄H₉ | CH₃ |
| 2-CO₂H | CH₃ | i-C₄H₉ | H |
| 2-CN | C₂H₅ | CH₃ | CH₃ |
| 2-CN | C₂H₅ | CH₃ | H |
| 2-CN | C₂H₅ | C₂H₅ | C₂H₅ |
| 2-CN | C₂H₅ | C₂H₅ | H |
| 3-CO₂H | —(CH₂)₅— | | H |
| 3-CO₂H | H | CH₃ | H |
| 3-CO₂H | HO(CH₂)— | C₂H₅ | H |
| 4-CO₂H | CF₃CH₂ | CH₃ | CH₃ |
| 4-CO₂H | CF₃CH₂ | CH₃ | H |
| 4-CO₂H | C₂H₅ | i-C₃H₇ | H |
| 4-CO₂H | —(CH₂)₆— | | CH₃ |
| 4-CO₂H | —(CH₂)₆— | | H |
| 4-CO₂H | CH₃ | cyclo C₆H₁₁ | C₂H₅ |
| 4-CO₂H | CH₃ | cyclo C₆H₁₁ | H |
| 4-CN | CH₃ | CH₃ | H |
| 4-CN | CH₃ | n-C₃H₇ | H |
| 4-CN | n-C₃H₇ | n-C₃H₇ | H |
| 4-CN | —(CH₂)₂S(CH₂)₂— | | n-C₃H₇ |
| 4-CN | —(CH₂)₂S(CH₂)₂— | | H |
| 4-CN | —(CH₂)₂N(CH₃)(CH₂)₂— | | H |

EXAMPLE XVI

4-Diethylamino-6-(m-nitrophenyl)pyrimidine hydrochloride

To a solution of 1.0 g. (3.8 m moles) of 4-diethylamino-6-phenylpyrimidine hydrochloride in 10 ml. of concentrated sulfuric acid is added 10 ml. of nitric acid dropwise at room temperature. The reaction mixture is allowed to stir for 6 hours, and is then poured onto ice and made basic with concentrated ammonium hydroxide. The product is extracted into chloroform, and the organic layer dried over sodium sulfate and concentrated in vacuo to an oil. The residual oil is dissolved in ethyl acetate and hydrogen chloride slowly introduced into the solution until the precipitation is complete. The hydrogen chloride salt is filtered, dried and recrystallized, m.p. 238°–240° C.

Anal. Calcd. for $C_{14}H_{16}O_2N_4 \cdot HCl$: C, 54.5; H, 5.6; N, 18.2. Found: C, 54.1; H, 5.6; N, 18.0.

EXAMPLE XVII

The nitration procedure of Example XVI is repeated, using the appropriate starting reagents, to provide the following analogs in good yields:

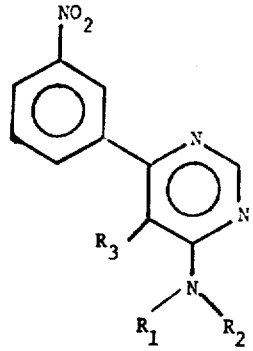

| R₁ | R₂ | R₃ | R₁ | R₂ | R₃ |
|----|----|----|----|----|----|
| H | C₂H₅ | H | CF₃CH₂ | H | H |
| H | i-C₃H₇ | H | CF₃CH₂ | C₂H₅ | H |
| H | n-C₄H₉ | H | H | (CH₃)₂N(CH₂)₂— | H |
| CH₃ | CH₃ | H | CH₃ | HO(CH₂)₂— | H |
| CH₃ | n-C₃H₇ | H | C₂H₅ | HO(CH₂)₂— | H |
| C₂H₅ | n-C₃H₇ | H | CH₃ | cyclo C₆H₁₁ | H |
| n-C₃H₇ | n-C₃H₇ | H | HO(CH₂)₂— | cyclo C₃H₅ | H |
| —(CH₂)₄— | | H | HO(CH₂)₂— | HO(CH₂)₂— | H |
| —(CH₂)₅— | | H | CH₂=CHCH₂ | CH₂=CHCH₂ | H |
| —(CH₂)₆— | | H | H | 2-HO₂CC₆H₄ | H |
| —(CH₂)₂O(CH₂)₂— | | H | H | 2-H₂NSO₂C₆H₄ | H |
| —(CH₂)₂N(CH₃)(CH₂)₂— | | H | CH₃ | cyclo C₃H₇ | CH₃ |
| C₂H₅ | C₂H₅ | CH₃ | CH₃ | cyclo C₆H₁₁ | C₂H₅ |
| i-C₃H₇ | i-C₃H₇ | CH₃ | CH₃ | CH₂=CHCH₂ | cyclo C₆H₁₁ | CH₃ |
| CH₃ | CH₃ | C₂H₅ | C₂H₅ | C₂H₅ | C₂H₅ |

| $R_1$ | $R_2$ | $R_3$ | $R_1$ | -continued $R_2$ | $R_3$ |
|---|---|---|---|---|---|
| $CH_3$ | $CH_3$ | | | $n\text{-}C_3H_7$ | |

EXAMPLE XVIII

The procedure of Example II is repeated, starting with the appropriate benzothieno[3,2-d]pyrimidine, to provide in moderate yields the following compounds:

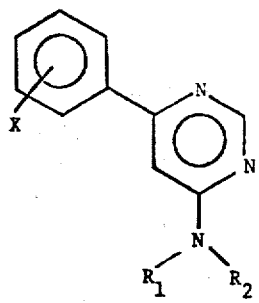

| X | $R_1$ | $R_2$ |
|---|---|---|
| 2-$NO_2$ | H | H |
| 2-$NO_2$ | $CH_3$ | H |
| 2-$NO_2$ | $C_2H_5$ | $C_2H_5$ |
| 2-$NO_2$ | $C_2H_5$ | $HO(CH_2)_2-$ |
| 2-$NO_2$ | $n\text{-}C_3H_7$ | $C_2H_5$ |
| 4-$NO_2$ | H | H |
| 4-$NO_2$ | $CH_3$ | $CH_3$ |
| 4-$NO_2$ | $C_2H_5$ | H |
| 4-$NO_2$ | $C_2H_5$ | $HO(CH_2)_2-$ |
| 4-$NO_2$ | $HO(CH_2)_2-$ | $HO(CH_2)_2-$ |
| 4-$NO_2$ | $n\text{-}C_3H_7$ | $n\text{-}C_3H_7$ |

EXAMPLE XIX

4-Diethylamino-6-(m-aminophenyl)pyrimidine dihydrochloride

A solution of 24.5 g. (0.8 mole) of 4-diethylamino-6-(m-nitrophenyl)pyrimidine hydrochloride, 62 g. of stannous chloride and 370 ml. of 12 N hydrochloric acid contained in a 2 l. 3-necked flask is heated and stirred for 3 hours at 60° C. and then allowed to stir at room temperature overnight. The precipitate is filtered, washed with 12 N hydrochloric acid and dissolved in water. The aqueous solution is made basic with 10% sodium hydroxide solution and extracted with chloroform. Separation of the organic layer followed by drying over sodium sulfate and concentration to dryness provides the crude product as an oil. The residue is redissolved in chloroform and treated with gaseous hydrogen chloride until a precipitate no longer forms. The product is filtered and dried, 19.1 g., m.p. 245°–247° C.

Mol wt.: Calcd. for 315.25. Found: 311. Equiv. wt.: Calcd. for 157.62. Found: 161.

The free base, generated by treating an aqueous solution of the hydrochloride salt with a 10% sodium hydroxide solution, has a melting point of 78° C.

Anal. Calcd. for $C_{14}H_{18}N_4$: C, 69.4; H, 7.5; N, 23.1. Found: C, 69.0; H, 7.5; N, 23.2.

EXAMPLE XX

The procedure of Example XIX is repeated, starting with the compounds of Examples XVII and XVIII, to synthesize the following congeners:

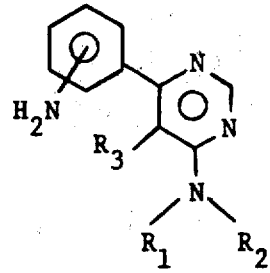

| $NH_2$-Position of Substitution | $R_1$ | $R_2$ | $R_3$ |
|---|---|---|---|
| 2 | H | H | H |
| 2 | $CH_3$ | H | H |
| 2 | $C_2H_5$ | $C_2H_5$ | H |
| 2 | $C_2H_5$ | $HO(CH_2)_2-$ | H |
| 2 | $n\text{-}C_3H_7$ | $C_2H_5$ | H |
| 3 | H | $C_2H_5$ | H |
| 3 | H | $i\text{-}C_3H_7$ | H |
| 3 | H | $n\text{-}C_4H_9$ | H |
| 3 | $CH_3$ | $CH_3$ | $C_2H_5$ |
| 3 | $CH_3$ | $CH_3$ | $n\text{-}C_3H_7$ |
| 3 | $CH_3$ | $n\text{-}C_4H_9$ | H |
| 3 | $C_2H_5$ | $n\text{-}C_4H_9$ | H |
| 3 | $n\text{-}C_3H_7$ | $n\text{-}C_4H_9$ | H |
| 3 | $-(CH_2)_4-$ | | H |
| 3 | $-(CH_2)_5-$ | | H |
| 3 | $-(CH_2)_6-$ | | H |
| 3 | $-(CH_2)_2O(CH_2)_2-$ | H | |
| 3 | $C_2H_5$ | $C_2H_5$ | $C_2H_5$ |
| 3 | $-(CH_2)_2N(CH_3)(CH_2)_2$ | H | |
| 3 | $CF_3CH_2$ | H | H |
| 3 | $CF_3CH_2$ | $C_2H_5$ | H |
| 3 | H | $(CH_3)_2N(CH_2)_2-$ | H |
| 3 | $CH_3$ | $HO(CH_2)_2-$ | H |
| 3 | $CH_3$ | cyclo $C_6H_{11}$ | $C_2H_5$ |
| 3 | $C_2H_5$ | $HO(CH_2)_2-$ | H |
| 3 | cyclo $C_3H_5$ | $HO(CH_2)_2-$ | H |
| 3 | $HO(CH_2)_2-$ | $HO(CH_2)_2-$ | H |
| 3 | $CH_2=CHCH_2$ | $CH_2=CHCH_2$ | H |
| 3 | H | 2-$HO_2CC_6H_4$ | H |

-continued

| NH$_2$-Position of Substitution | R$_1$ | R$_2$ | R$_3$ |
|---|---|---|---|
| 3 | H | 2-H$_2$NSO$_2$C$_6$H$_4$ | H |
| 4 | H | H | H |
| 4 | CH$_3$ | CH$_3$ | H |
| 4 | C$_2$H$_5$ | H | H |
| 4 | C$_2$H$_5$ | HO(CH$_2$)$_2$— | H |
| 4 | HO(CH$_2$)$_2$— | HO(CH$_2$)$_2$— | H |
| 4 | n-C$_3$H$_7$ | n-C$_3$H$_7$ | H |

EXAMPLE XXI

4-Diethylamino-6-(m-acetylaminopheny)pyrimidine hydrochloride

Acid Chloride Method

To a suspension of 2.3 g. of sodium carbonate in 140 ml. of ether containing 5.1 g. (0.021 mole) of 4-Diethylamino-6-(m-aminophenyl)pyrimidine is slowly added 1.6 g. of acetyl chloride in 20 ml. of the same solvent. The reaction mixture is stirred for 24 hours and is then treated with water. The ether layer is separated, dried over sodium sulfate and concentrated in vacuo to an oil, which is taken up in ethyl acetate and treated with gaseous hydrogen chloride until a precipitate no longer forms. The product is filtered and recrystallized from ethyl acetate/methanol, 2.1 g., m.p. 236°–238° C.

Anal. Calcd. for C$_{16}$H$_{20}$ON$_4$.HCl: C, 54.5; H, 5.6; N, 17.9. Found: C, 54.1; H, 5.6; N, 18.0.

Anhydride Method

To 5.6 g. (0.022 mole) of 4-diethylamino-6-(m-aminophenyl)pyrimidine is slowly added, with cooling, 25 ml. of acetic anhydride. The resulting solution is stirred overnight at room temperature and is then diluted with 500 ml. of ethyl acetate amd treated with sufficient gaseous hydrogen chloride to complete the precipitation of the desired product. The solvent and excess acetic anhydride are removed under reduced pressure and the residue washed from the flask with 20 ml. of 1:1 hexane/ethyl acetate 6.6 g., m.p. 235°–237° C. It proves to be identical to that prepared by the Acid Chloride Method.

EXAMPLE XXII

Starting with the suitably substituted 6-aminophenyl-pyrimidine and requisite reagents and following the appropriate procedure method in Example XXI the following compounds are prepared:

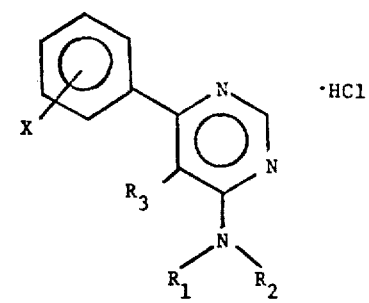

| Method | X | R$_1$ | R$_2$ | R$_3$ | m.p., °C. |
|---|---|---|---|---|---|
| Anhydride | 3-NHCOCH$_3$ | n-C$_3$H$_7$ | n-C$_3$H$_7$ | H | 128–129 |
| Anhydride | 3-NHCOCH$_3$ | —(CH$_2$)$_4$— | | H | 289–291 |
| Anhydride | 3-NHCOCH$_3$ | n-C$_4$H$_9$ | n-C$_4$H$_9$ | H | 193–195 |
| Acid Chloride | 3-NHCOC$_2$H$_5$ | C$_2$H$_5$ | C$_2$H$_5$ | H | 232–234 |
| Acid Chloride | 3-NHCO(CH$_2$)$_2$CH$_3$ | C$_2$H$_5$ | C$_2$H$_5$ | H | 215–218 |
| Acid Chloride | 3-NHCOCH(CH$_3$)$_2$ | C$_2$H$_5$ | C$_2$H$_5$ | H | 248–250 |
| Acid Chloride | 3-NHCOCF$_3$ | C$_2$H$_5$ | C$_2$H$_5$ | H | 149–151 |
| Acid Chloride | 3-NHCOC$_6$H$_5$ | C$_2$H$_5$ | C$_2$H$_5$ | H | 230–234 |
| Acid Chloride | 3-NHCO$_2$CH$_3$ | C$_2$H$_5$ | C$_2$H$_5$ | H | 223 dec. |
| Acid Chloride | 3-NHCO$_2$C$_2$H$_5$ | C$_2$H$_5$ | C$_2$H$_5$ | H | 224 dec. |
| Acid Chloride | 3-NHSO$_2$CH$_3$ | C$_2$H$_5$ | C$_2$H$_5$ | H | 225 |
| Acid Chloride | 3-NHSO$_2$CH$_3$ | n-C$_3$H$_7$ | n-C$_3$H$_7$ | H | 205 |
| Anhydride | 4-NHCOCH$_3$ | C$_2$H$_5$ | C$_2$H$_5$ | H | 272–275 dec. |
| Anhydride | 3-NHCOCH$_3$ | CH$_3$ | CH$_3$ | C$_2$H$_5$ | 215–217 |
| Anhydride | 3-NHCOCH$_3$ | C$_2$H$_5$ | C$_2$H$_5$ | CH$_3$ | 174–176 |
| Anhydride | 3-NHCOCH$_3$ | C$_2$H$_5$ | C$_2$H$_5$ | C$_2$H$_5$ | 136–138 |
| Anhydride | 3-NHCOCH$_3$ | n-C$_3$H$_7$ | n-C$_3$H$_7$ | CH$_3$ | 198–202 |
| Anhydride | 3-NHCOCH$_3$ | C$_2$H$_5$ | C$_2$H$_5$ | n-C$_3$H$_7$ | 173–175 |

EXAMPLE XXIII

The procedure of Example XXI is repeated, using the appropriate starting materials, to provide the following analogs:

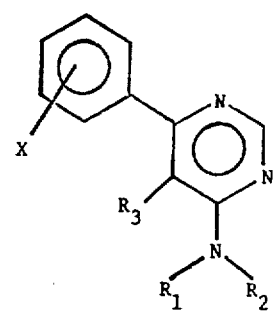

| Method | X | R$_1$ | R$_2$ | R$_3$ |
|---|---|---|---|---|
| Anhydride | 2-NHCOCH$_3$ | C$_2$H$_5$ | C$_2$H$_5$ | H |

-continued

| Method | X | R₁ | R₂ | R₃ |
|---|---|---|---|---|
| Anhydride | 2-NHCOCH₃ | C₂H₅ | n-C₃H₇ | H |
| Anhydride | 2-NHCO(CH₂)₂CH₃ | C₂H₅ | n-C₃H₇ | H |
| Anhydride | 2-NHCOCH(CH₃)₂ | C₂H₅ | C₂H₅ | H |
| Acid Chloride | 2-NHSO₂CH₃ | C₂H₅ | C₂H₅ | H |
| Acid Chloride | 3-NHSO₂C₆H₅ | CH₃ | CH₃ | C₂H₅ |
| Acid Chloride | 3-NHCOCH₂CH₃ | —(CH₂)₅— | H | |
| Anhydride | 3-NHCOCH₃ | H | 2-HO₂CC₆H₄ | H |
| Anhydride | 3-NHCOCH₃ | H | 2-H₂NSO₂C₆H₄ | H |
| Anhydride | 4-NHCOCH₃ | CH₃ | CH₃ | H |
| Anhydride | 4-NHCOCH₂CH₃ | CH₃ | CH₃ | H |
| Acid Chloride | 4-NHCOCH(CH₃)₂ | CH₃ | CH₃ | H |
| Anhydride | 4-NHCOCH₃ | n-C₃H₇ | n-C₃H₇ | H |
| Anhydride | 4-NHCHO | n-C₃H₇ | n-C₃H₇ | H |
| Acid Chloride | 4-NHSO₂CH₃ | CH₃ | CH₃ | H |
| Acid Chloride | 4-NHCO₂C₂H₅ | CH₃ | CH₃ | H |
| Acid Chloride | 4-NHCOC₆H₅ | n-C₃H₇ | n-C₃H₇ | H |
| Anhydride | 3-NHCOCH₃ | C₂H₅ | C₂H₅ | C₂H₅ |
| Anhydride | 3-NHCOCH₃ | CH₃ | CH₃ | C₂H₅ |

EXAMPLE XXIV

4-Diethylamino-6-(m-dimethylaminophenyl)pyrimidine hydrochloride

To a solution of 2.6 g. (9.3 m moles) of 4-diethylamino-6-(m-aminophenyl)pyrimidine hydrochloride in 50 ml. of water is added 4.72 g. of sodium carbonate followed by the slow addition of 2.74 g. of methyl iodide. The reaction mixture is heated to the reflux temperature for 6 hours, and is then cooled and extracted with chloroform. The organic layer is separated, dried over sodium sulfate and evaporated in vacuo to a light brown oil. Chromatographing on a silica gel column and eluting with ethyl acetate provides the desired product as a light yellow oil which when dissolved in ethyl acetate and treated with gaseous hydrogen chloride provides the corresponding crude hydrochloride salt. Further purification is effected by recrystallization from methanol/ethyl acetate, 0.9 g., m.p. 170°–173° C.

EXAMPLE XXV

Following the procedure of Example XXIV, and starting with the requisite 6-aminophenylpyrimidine and appropriate reagents, the following compounds are synthesized:

| X | R₁ | R₂ | R₃ |
|---|---|---|---|
| 2-N(CH₃)₂ | C₂H₅ | C₂H₅ | H |
| 2-N(CH₃)₂ | C₂H₅ | HO(CH₂)₂— | H |
| 2-N(CH₃)₂ | C₂H₅ | n-C₃H₇ | H |
| 2-N(C₂H₅)₂ | C₂H₅ | C₂H₅ | H |
| 2-N(C₃H₇)₂ | C₂H₅ | HO(CH₂)₂— | H |
| 3-N(CH₃)₂ | CH₃ | CH₃ | H |
| 3-N(CH₃)₂ | C₂H₅ | HO(CH₂)₂— | H |
| 3-N(CH₃)₂ | C₂H₅ | n-C₃H₇ | H |
| 3-N(CH₃)₂ | CF₃CH₂ | H | H |
| 3-N(CH₃)₂ | —(CH₂)₆— | | H |
| 3-N(n-C₃H₇)₂ | —(CH₂)₂O(CH₂)₂— | | H |
| 3-N(n-C₃H₇)₂ | C₂H₅ | HO(CH₂)₂— | H |
| 3-N(CH₃)₂ | CH₃ | CH₃ | C₂H₅ |
| 3-N(C₂H₅)₂ | CH₃ | CH₃ | n-C₃H₇ |
| 3-N(CH₃)₂ | C₂H₅ | C₂H₅ | C₂H₅ |
| 3-N(n-C₃H₇)₂ | CF₃CH₂ | H | H |
| 3-N(n-C₃H₇)₂ | CH₃ | cyclo C₆H₁₁ | H |
| 4-N(CH₃)₂ | CH₃ | CH₃ | H |
| 4-N(CH₃)₂ | C₂H₅ | HO(CH₂)₂— | H |
| 4-N(CH₃)₂ | n-C₃H₇ | n-C₃H₇ | H |

-continued

| X | R₁ | R₂ | R₃ |
|---|---|---|---|
| 4-N(CH₃)₂ | CH₃ | H | H |
| 4-N(C₂H₅)₂ | CH₃ | CH₃ | H |
| 4-N(C₂H₅)₂ | C₂H₅ | HO(CH₂)₂— | H |
| 4-N(n-C₃H₇)₂ | C₂H₅ | HO(CH₂)₂— | H |
| 4-N(n-C₃H₇)₂ | n-C₃H₇ | n-C₃H₇ | H |

EXAMPLE XXVI

Starting with 2-bromothiophene and the requisite reagents, and following the procedure of Example I, the following congeners are prepared:

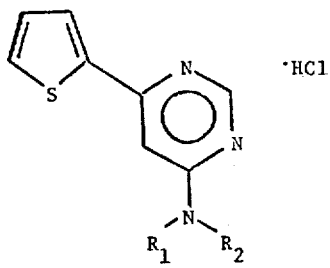

| R₁ | R₂ | m.p., °C. |
|---|---|---|
| H | H | 204–205 |
| CH₃ | H | 238–240 |
| C₂H₅ | H | 208–210 |
| CF₃CH₂ | H | 110 |
| CH₃ | CH₃ | 256–257 |
| C₂H₅ | C₂H₅ | 153–155 |
| CF₃CH₂ | C₂H₅ | 158–161 |
| n-C₃H₇ | n-C₃H₇ | 147–148 |
| CH₂=CHCH₂ | CH₂=CHCH₂ | 151–152 |
| CH₃ | HO(CH₂)₂— | 196–198 |
| C₂H₅ | HO(CH₂)₂— | 175–176 |
| HO(CH₂)₂— | HO(CH₂)₂— | 175–177 |

In a similar manner are prepared 4-ethylamino-5-methyl-6-(2-thienyl)-pyrimidine, 4-dimethylamino-5-ethyl-6-(3-thienyl)pyrimidine, 4-dipropyl-5-n-propyl-6-(3-thienyl)pyrimidine and 4-diallylamino-5-ethyl-6-(3-thienyl)pyrimidine.

EXAMPLE XXVII

4-Diethylamino-6-(5-acetylamino-2-thienyl)pyrimidine hydrochloride

A mixture of 28.26 g. (0.09 mole) of 4-diethylamino-6-(5-nitro-2-thienyl)pyrimidine hydrochloride and 35 g. of granular tin is treated, portionwise, with 75 ml. of concentrated hydrochloric acid. Cooling is necessary once the reaction has started. When the reaction has subsided, the clear hot solution is decanted from the unreacted tin and cooled in a salt-ice bath, and the resulting amine hydrochloride-stannic chloride complex which precipitates is filtered.

The complex is added to 75 ml. of water and 80 ml. of diethyl ether, and treated with sufficient sodium hydroxide to provide a pH of 9–10. The ether layer is separated, treated with 14.8 g. (0.135 mole) of acetic anhydride and heated to reflux for 3 hours. The resulting solution is washed with 5% sodium hydroxide solution, separated, dried over sodium sulfate and concentrated to dryness. The product is dissolved in ethyl acetate and sufficient hydrogen chloride gas bubbled into the solution to precipitate the product as the hydrochloride salt. Recrystallization from isopropanol provides the pure product.

EXAMPLE XXVIII

Employing the procedure of Example XXVII, and starting with the appropriate reagents, the following compounds are synthesized:

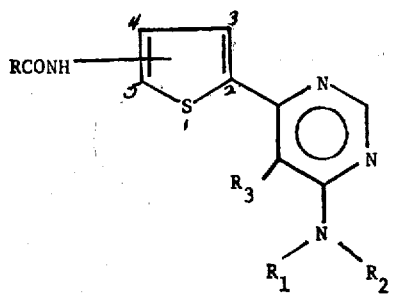

| Position of RCONH Substituent | R | $R_1$ | $R_2$ | $R_3$ |
|---|---|---|---|---|
| 3 | $CH_3$ | $n\text{-}C_3H_7$ | $n\text{-}C_3H_7$ | H |
| 3 | $C_2H_5$ |  | $-(CH_2)_6-$ | H |
| 3 | $C_2H_5$ | $C_2H_5$ | $CF_3CH_2$ | H |
| 3 | $C_2H_5$ | $CH_3$ | $CH_3$ | H |

-continued

| Position of RCONH Substituent | R | $R_1$ | $R_2$ | $R_3$ |
|---|---|---|---|---|
| 4 | $CH_3$ | $C_2H_5$ | $CF_3CH_2$ | H |
| 4 | H | $CH_3$ | $CH_3$ | H |
| 4 | $C_2H_5$ | $C_2H_5$ | $C_2H_5$ | H |
| 4 | $i\text{-}C_3H_7$ | $C_2H_5$ | $C_2H_5$ | H |
| 5 | $CH_3$ | $CH_3$ | $CH_3$ | H |
| 5 | $C_2H_5$ | $CH_3$ | $CH_3$ | H |
| 5 | $CH_3$ | $C_2H_5$ | $CF_3CH_2$ | H |
| 5 | $n\text{-}C_3H_7$ | $C_2H_5$ | $CF_3CH_2$ | H |
| 3 | $CH_3$ | $C_2H_5$ | H | $CH_3$ |
| 3 | $C_2H_5$ | $CH_3$ | $CH_3$ | $C_2H_5$ |
| 3 | $i\text{-}C_3H_7$ | $CH_3$ | $CH_3$ | $C_2H_5$ |
| 5 | $CH_3$ | $CH_3$ | $CH_3$ | $C_2H_5$ |
| 5 | $CH_3$ | $C_2H_5$ | H | $CH_3$ |

EXAMPLE XXIX

The procedure of Example III is repeated, starting with the appropriate reagents, to provide the following congeners in good yields:

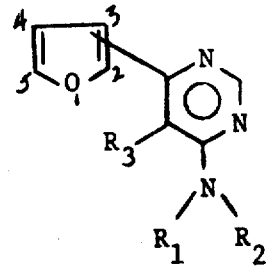

| Position of Substitution | $R_1$ | $R_2$ | $R_3$ |
|---|---|---|---|
| 2 | $CH_3$ | $CH_3$ | H |
| 2 | $CH_3$ | $CH_3$ | $C_2H_5$ |
| 2 | $n\text{-}C_3H_7$ | $C_2H_5$ | H |
| 2 | $HO(CH_2)_2-$ | $C_2H_5$ | H |
| 2 | $CF_3CH_2$ | $C_2H_5$ | H |
| 2 | H | $HO_2CC_6H_4-$ | H |
| 2 | H | $H_2NSO_2C_6H_4-$ | H |
| 3 | H | $n\text{-}C_3H_7$ | H |
| 3 | $CH_3$ | $C_2H_5$ | H |
| 3 | $CH_3$ | $C_2H_5$ | $C_2H_5$ |
| 3 | $C_2H_5$ | $C_2H_5$ | H |
| 3 | $CF_3CH_2$ | $C_2H_5$ | H |
| 3 |  | $-(CH_2)_5-$ | H |
| 3 | H | $HO_2CC_6H_4-$ | H |
| 3 | $CH_3$ | $(CH_3)_2N(CH_2)_2-$ | $CH_3$ |
| 3 | $CH_3$ | $(CH_3)_2N(CH_2)_2-$ | H |

EXAMPLE XXX

The procedure of Example III is again repeated, using the requisite starting reagents, to provide, in good yields, the following products:

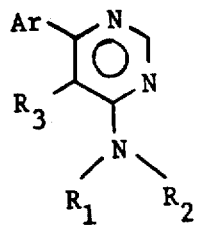

| Ar | $R_1$ | $R_2$ | $R_3$ |
|---|---|---|---|
| 1-naphthyl | $C_2H_5$ | $C_2H_5$ | H |
| 1-naphthyl | $n\text{-}C_3H_7$ | $C_2H_5$ | H |
| 1-naphthyl | $CF_3CH_2$ | $C_2H_5$ | H |
| 1-naphthyl | $CF_3CH_2$ | $C_2H_5$ | $C_2H_5$ |
| 1-naphthyl | $HO(CH_2)_2-$ | $C_2H_5$ | H |
| 2-naphthyl | H | H | H |

-continued

| Ar | R₁ | R₂ | R₃ |
|---|---|---|---|
| 2-naphthyl | $C_2H_5$ | $C_2H_5$ | $C_2H_5$ |
| 2-naphthyl | n-$C_3H_7$ | n-$C_3H_7$ | H |
| 2-naphthyl | $(CH_3)_2N(CH_2)_2$ | H | H |
| 2-naphthyl | $C_2H_5$ | $CF_3CH_2$ | H |
| 2-naphthyl | $-(CH_2)_2N(C_2H_5)(CH_2)_2-$ | H | H |
| 2-naphthyl | H | $HO_2CC_6H_4$ | H |
| 2-indolyl | $CH_3$ | H | H |
| 2-indolyl | $CH_3$ | $CH_3$ | H |
| 2-indolyl | $CH_3$ | $CH_3$ | $CH_3$ |
| 2-indolyl | $C_2H_5$ | $CF_3CH_2$ | H |
| 2-indolyl | $CH_2-CHCH_2$ | $C_2H_5$ | H |
| 2-indolyl | $HO(CH_2)_2-$ | $C_2H_5$ | $CH_3$ |
| 2-indolyl | $HO(CH_2)_2-$ | $C_2H_5$ | H |
| 2-indolyl | i-$C_3H_7$ | i-$C_3H_7$ | H |
| 3-indolyl | $CH_3$ | $CH_3$ | H |
| 3-indolyl | $-(CH_2)_2O(CH_2)_2-$ |  | H |
| 3-indolyl | $C_2H_5$ | $C_2H_5$ | H |
| 3-indolyl | H | $HO_2CC_6H_4$ | H |
| 3-indolyl | H | $H_2NSO_2C_6H_4$ | H |
| 3-indolyl | H | $H_2NSO_2C_6H_4$ | $C_2H_5$ |
| 2-benzofuryl | $CH_3$ | $C_2H_5$ | H |
| 2-benzofuryl | $HO(CH_2)_2-$ | $C_2H_5$ | H |
| 2-benzofuryl | $CF_3CH_2$ | $C_2H_5$ | H |
| 2-benzofuryl | $CF_3CH_2$ | $C_2H_5$ | n-$C_3H_7$ |
| 2-benzofuryl | $(CH_3)_2N(CH_2)_2-C_2H_5$ |  | H |
| 2-benzofuryl | $-(CH_2)_6-$ |  | H |
| 3-benzofuryl | $CH_3$ | $CH_3$ | H |
| 3-benzofuryl | $C_2H_5$ | cyclo $C_3H_5$ | H |
| 3-benzofuryl | $C_2H_5$ | $C_2H_5$ | H |
| 3-benzofuryl | $C_2H_5$ | $C_2H_5$ | i-$C_3H_7$ |
| 3-benzofuryl | $-(CH_2)_2S(CH_2)_2-$ |  | H |
| 3-benzofuryl | i-$C_3H_7$ | i-$C_3H_7$ | H |
| 3-benzofuryl | $CH_3$ | cyclo $C_7H_{13}$ | H |

EXAMPLE XXXI

The procedure of Example I is repeated, starting with the appropriate 2- or 3-halobenzo[b]thiophene and requisite reagents to provide the following compounds in moderately good yields;

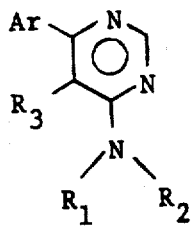

| Ar | R₁ | R₂ | R₃ |
|---|---|---|---|
| 2-benzothienyl | $CH_3$ | H | H |
| 2-benzothienyl | $C_2H_5$ | $CH_3$ | H |
| 2-benzothienyl | $C_2H_5$ | $CH_3$ | $CH_3$ |
| 2-benzothienyl | $C_2H_5$ | $CF_3CH_2$ | H |
| 2-benzothienyl | $CH_3$ | cyclo $C_5H_9$ | H |
| 2-benzothienyl | $CH_3$ | cyclo $C_6H_{11}$ | H |
| 3-benzothienyl | $CH_3$ | $CH_3$ | H |
| 3-benzothienyl | $CH_3$ | $CH_3$ | $C_2H_5$ |
| 3-benzothienyl | $C_2H_5$ | $HO(CH_2)_2-$ | H |
| 3-benzothienyl | $C_2H_5$ | $CF_3CH_2$ | H |
| 3-benzothienyl | H | $HO_2CC_6H_4$ | H |
| 3-benzothienyl | H | $H_2NSO_2C_6H_4$ | H |
| 3-benzothienyl | H | $(CH_3)_2N(CH_2)_2-$ | H |
| 3-benzothienyl | $CH_2=CHCH_2$ | $CH_2=CHCH_2$ | H |

EXAMPLE XXXII

4-Diethylamino-6-(5-acetylamino-2-furyl)pyrimidine hydrochloride

To a mixture of 2.62 g. (0.01 mole) of 4-diethylamino-6-(5-nitro-2-furyl)pyrimidine and aluminum amalgam, prepared from 4.0 g. of aluminum turnings, in 60 ml. of diethyl ether is added 4 ml. of water. Acetic anhydride (2.0 g.; 0.02 mole) is added dropwise during the ensuing reaction which is maintained by heating the reaction vessel in a warm water bath. The ether is filtered and the filtrate dried over sodium sulfate. Removal of the solvent under reduced pressure provides the crude product. The residue is dissolved in ethyl acetate and treated with gaseous hydrogen chloride until a precipitate no longer forms. The resulting hydrochloride salt is further purified by several recrystallizations form methanol/hexane.

EXAMPLE XXXIII

The reduction-acylation procedure of Example XXXII is repeated, using the appropriately substituted starting materials, to provide the following analogs:

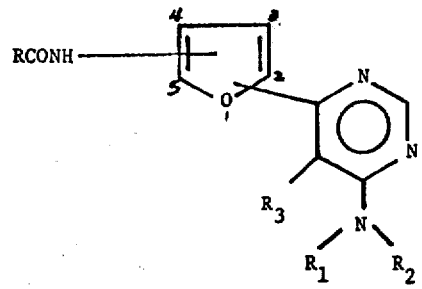

| Position of Substitution RCONH— | furyl | R | R₁ | R₂ | R₃ |
|---|---|---|---|---|---|
| 3 | 2 | $C_2H_5$ | $C_2H_5$ | $C_2H_5$ | H |
| 3 | 2 | $CH_3$ | $C_2H_5$ | $C_2H_5$ | H |
| 4 | 2 | $CH_3$ | $CF_3CH_2$ | $C_2H_5$ | H |
| 4 | 2 | n-$C_3H_7$ | $CF_3CH_2$ | $C_2H_5$ | H |
| 5 | 2 | $C_2H_5$ | $C_2H_5$ | $C_2H_5$ | H |
| 5 | 2 | i-$C_3H_7$ | $C_2H_5$ | $C_2H_5$ | H |
| 2 | 3 | $CH_3$ | $CH_3$ | $C_2H_5$ | H |
| 2 | 3 | $C_2H_5$ | $CF_3CH_2$ | $C_2H_5$ | H |
| 4 | 3 | $CH_3$ | $CF_3CH_2$ | $C_2H_5$ | H |
| 4 | 3 | $CH_3$ | $-(CH_2)_5-$ |  | H |
| 4 | 3 | $C_2H_5$ | $-(CH_2)_5-$ |  | H |

-continued

| Position of Substitution RCONH— | furyl | R | R₁ | R₂ | R₃ |
|---|---|---|---|---|---|
| 5 | 3 | CH₃ | CH₃ | C₂H₅ | H |
| 5 | 3 | C₂H₅ | CF₃CH₂ | C₂H₅ | H |
| 5 | 3 | CH₃ | —(CH₂)₅— | | H |
| 5 | 2 | CH₃ | CH₃ | CH₃ | C₂H₅ |
| 5 | 2 | C₂H₅ | CH₃ | CH₃ | C₂H₅ |
| 5 | 3 | CH₃ | CH₃ | C₂H₅ | C₂H₅ |

EXAMPLE XXXIV

The procedures of Examples XIX and XXI are repeated, using the requisite starting reagents, to provide the following compounds in moderate yields:

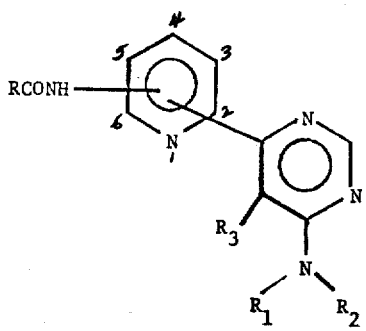

| Position of Substitution RCONH | pyridyl | R | R₁ | R₂ | R₃ |
|---|---|---|---|---|---|
| 3 | 2 | CH₃ | CH₃ | CH₃ | H |
| 4 | 2 | CH₃ | C₂H₅ | C₂H₅ | H |
| 4 | 2 | C₂H₅ | C₂H₅ | C₂H₅ | H |
| 4 | 2 | CH₃ | CF₃CH₂ | C₂H₅ | H |
| 5 | 2 | CH₃ | C₂H₅ | C₂H₅ | H |
| 4 | 3 | CH₃ | C₂H₅ | C₂H₅ | H |
| 5 | 3 | CH₃ | C₂H₅ | C₂H₅ | H |
| 5 | 3 | C₂H₅ | —(CH₂)₅— | | H |
| 5 | 3 | CH₃ | CF₃CH₂ | C₂H₅ | H |
| 6 | 3 | CH₃ | CH₃ | cyclo C₆H₁₁ | H |
| 2 | 4 | CH₃ | C₂H₅ | C₂H₅ | H |
| 2 | 4 | n-C₃H₉ | CH₃ | CH₃ | H |
| 2 | 4 | i-C₃H₇ | C₂H₅ | C₂H₅ | H |
| 2 | 4 | CH₃ | CF₃CH₂ | C₂H₅ | H |
| 3 | 4 | CH₃ | —(CH₂)₂O(CH₂)₂— | | H |
| 3 | 4 | C₂H₅ | C₂H₅ | C₂H₅ | H |
| 3 | 4 | H | C₂H₅ | C₂H₅ | H |
| 4 | 2 | CH₃ | CH₃ | CH₃ | C₂H₅ |
| 4 | 2 | C₂H₅ | C₂H₅ | C₂H₅ | C₂H₅ |
| 5 | 2 | n-C₃H₉ | CH₃ | C₂H₅ | CH₃ |
| 5 | 2 | CH₃ | H | CF₃CH₂ | n-C₃H₇ |

EXAMPLE XXXV

4-Diethylamino-6-(2-furyl)pyrimidine hydrochloride

Crude 4-diethylamino-6-(2furyl)pyrimidine (3.2 g.; 0.015 mole), obtained by repeating the procedures of Example III, is dissolved in 25 ml. of dry ethyl acetate and treated with 1.44 g. (0.016 mole) of oxalic acid. The resulting solution is warmed briefly on a steam bath, and is then cooled in a salt-ice bath. The resulting oxalate salt is filtered, dried and recrystallized from methanol/hexane. The purified oxalate is dissolved in a minimum amount of water and the pH adjusted to 9 using a 5% sodium hydroxide solution. Ethyl acetate is added and the free base rapidly extracted. The organic phase is dried over sodium sulfate and treated with sufficient gaseous hydrogen chloride to completely precipitate the hydrochloride salt, which is filtered, washed with acetone and dried, m.p. 179°–180°C.

EXAMPLE XXXVI

Starting with the appropriately substituted reagents and employing the respective procedures indicated, the following products are synthesized;

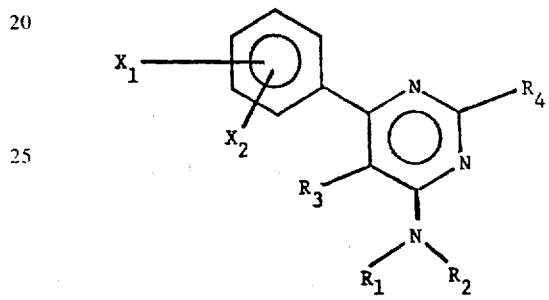

| X₁ | X₂ | R₁ | R₂ | R₃ | R₄ | Procedure |
|---|---|---|---|---|---|---|
| 3-CH₃CO | H | CH₃ | CH₃ | H | H | Example III |
| 3-CH₃CO | H | C₂H₅ | C₂H₅ | H | H | Example III |
| 3-CH₃CO | H | —(CH₂)₅— | | H | H | Example III |
| 4-CH₃CO | H | CF₃CH₂ | C₂H₅ | CH₃ | H | Example III |
| 4-CH₃CO | H | HO(CH₂)₂— | C₂H₅ | CH₃ | H | Example III |
| 4-CH₃CO | H | H | HO₂CC₆H₄ | CH₃ | H | Example III |
| 4-CH₃CO | H | —(CH₂)₄— | | CH₃ | H | Example III |
| 3,4-CH₂O₂ | | C₂H₅ | C₂H₅ | H | H | Example I |
| 3,4-CH₂O₂ | | HO(CH₂)₂— | C₂H₅ | H | H | Example I |
| 3,4-CH₂O₂ | | CF₃CH₂ | C₂H₅ | H | H | Example I |
| 3,4-CH₂O₂ | | CH₂=CHCH₂ | C₂H₅ | H | H | Example I |
| 3-NO₂ | 4-Cl | C₂H₅ | C₂H₅ | H | H | Example XVI |
| 3-NO₂ | 4-Cl | CF₃CH₂ | C₂H₅ | H | H | Example XVI |
| 3-NO₂ | 4-OCH₃ | CF₃CH₂ | C₂H₅ | H | H | Example XVI |

-continued

| $X_1$ | $X_2$ | $R_1$ | $R_2$ | $R_3$ | $R_4$ | Procedure |
|---|---|---|---|---|---|---|
| 3-$NO_2$ | 4-$OCH_3$ | $C_2H_5$ | $C_2H_5$ | H | H | Example XVI |
| 3-$NO_2$ | 4-F | —$(CH_2)_5$— | | H | H | Example XVI |
| 3-$NH_2$ | 4-Cl | $C_2H_5$ | $C_2H_5$ | H | H | Example XIX |
| 3-$NH_2$ | 4-Cl | $CF_3CH_2$ | $C_2H_5$ | H | H | Example XIX |
| 3-$NH_2$ | 4-$OCH_3$ | $CF_3CH_2$ | $C_2H_5$ | H | H | Example XIX |
| 3-$NH_2$ | 4-$OCH_3$ | $C_2H_5$ | $C_2H_5$ | H | H | Example XIX |
| 3-$NH_2$ | 4-F | —$(CH_2)_5$— | | H | H | Example XIX |
| 3-$CH_3CONH$ | 4-Cl | $C_2H_5$ | $C_2H_5$ | H | H | Example XXI |
| 3-$CH_3CONH$ | 4-Cl | $CF_3CH_2$ | $C_2H_5$ | H | H | Example XXI |
| 3-$CH_3CONH$ | 4-$OCH_3$ | $CF_3CH_2$ | $C_2H_5$ | H | H | Example XXI |
| 3-$CH_3CONH$ | 4-$OCH_3$ | $C_2H_5$ | $C_2H_5$ | H | H | Example XXI |
| 3-$CH_3CONH$ | 4-F | —$(CH_2)_5$— | | H | H | Example XXI |
| 3-$CH_3O_2CNH$ | 4-Cl | $C_2H_5$ | $C_2H_5$ | H | H | Example XXI |
| 3-$C_2H_5O_2CNH$ | 4-$OCH_3$ | $C_2H_5$ | $C_2H_5$ | H | H | Example XXI |
| 3-$C_2H_5O_2CNH$ | 4-F | —$(CH_2)_5$— | | H | H | Example XXI |
| 3-$CH_3CONH$ | H | $C_2H_5$ | $C_2H_5$ | $CH_3$ | $CH_3$ | Example I |
| 3-$CH_3CONH$ | H | $C_2H_5$ | $CF_3CH_2$ | $CH_3$ | $CH_3$ | Example I |
| 3-$CH_3CONH$ | H | $C_2H_5$ | $C_2H_5$ | H | $C_2H_5$ | Example I |
| 3-$(CH_3)_2NCO$ | H | $C_2H_5$ | $C_2H_5$ | H | H | Example XXI |
| 3-$(C_2H_5)NCO$ | H | $C_2H_5$ | $C_2H_5$ | H | H | Example XXI |

EXAMPLE XXXVII

1-[3-(6-Diethylamino-4-pyrimidinyl)phenyl]-3-phenylurea hydrochloride

To 2.6 g. (0.011 mole) of 4-diethylamino-6-(m-aminophenyl)pyrimidine in 40 ml. of ether is added dropwise 1.3 g. of phenylisocyanate dissolved in 40 ml. of the same solvent, and the resulting mixture allowed to stir overnight at room temperature. Removal of the solvent under reduced pressure provides the crude product, 3.4 g., which is recrystallized from ethyl acetate/methanol, 2.3 g., m.p. 183°–184°C.

Anal. Calcd. for $C_{21}H_{23}ON_5$: C, 69.8; H, 6.4; N, 19.4. Found: C, 69.8; H, 6.5; N, 19.6.

EXAMPLE XXXVIII

The procedure of Example XXXVII is repeated, using the appropriate starting reagents, to provide the following analogs in good yields:

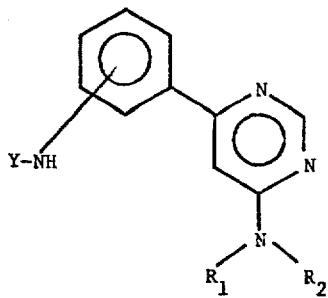

| Y | $R_1$ | $R_2$ |
|---|---|---|
| 2-$CH_3NHCO$ | $C_2H_5$ | $C_2H_5$ |
| 2-φNHCO | $C_2H_5$ | $C_2H_5$ |
| 2-φNHCS | $C_2H_5$ | $C_2H_5$ |
| 2-$CH_3NHCO$ | n-$C_3H_7$ | $C_2H_5$ |
| 3-φNHCO | $CH_3$ | $CH_3$ |
| 3-$CH_3NHCO$ | $CH_3$ | $CH_3$ |
| 3-$CH_3NHCO$ | n-$C_4H_9$ | $CH_3$ |
| 3-φNHCO | n-$C_4H_9$ | $C_2H_5$ |
| 3-$C_2H_5NHCO$ | $C_2H_5$ | $C_2H_5$ |
| 3-$C_2H_5NHCO$ | —$(CH_2)_2O(CH_2)_2$— | |
| 3-φNHCO | $CF_3CH_2$ | $C_2H_5$ |
| 3-$CH_3NHCO$ | $CF_3CH_2$ | $C_2H_5$ |
| 4-$CH_3NHCO$ | $CH_3$ | $CH_3$ |
| 4-φNHCO | $CH_3$ | $CH_3$ |
| 4-φNHCS | $CH_3$ | $CH_3$ |
| 4-$CH_3NHCO$ | n-$C_3H_7$ | n-$C_3H_7$ |
| 4-$C_2H_5NHCO$ | n-$C_3H_7$ | n-$C_3H_7$ |

-continued

| Y | $R_1$ | $R_2$ |
|---|---|---|
| 4-φNHCO | n-$C_3H_7$ | n-$C_3H_7$ |

EXAMPLE XXXLX

Tablets

A tablet base is prepared by blending the following ingredients in the proportion by weight indicated:

| | |
|---|---|
| Sucrose, U.S.P. | 80.3 |
| Tapioca starch | 13.2 |
| Magnesium stearate | 6.5 |

Into this tablet base there is blended sufficient 4-diethylamino-6-(m-acetylaminophenyl)pyrimidine hydrochloride to provide tablets containing 20, 100 and 250 mg. of active ingredient per tablet. The compositions are each compressed into tablets, each weighing 360 mg., by conventional means.

EXAMPLE XL

Capsules

A blend is prepared containing the following ingredients:

| | |
|---|---|
| Calcium carbonate, U.S.P. | 17.6 |
| Dicalcium phosphate | 18.8 |
| Magnesium trisilicate, U.S.P. | 5.2 |
| Lactose, U.S.P. | 5.2 |
| Potato starch | 5.2 |
| Magnesium stearate A | 0.8 |
| Magnesium stearate B | 0.35 |

To this blend is added sufficient 4-diethylamino-6-(m-dimethylaminophenyl)pyrimidine hydrochloride to provide capsules containing 20, 100 and 250 mg. of active ingredient per capsule. The compositions are filled into conventional hard gelatin capsules in the amount of 350 mg. per capsule.

EXAMPLE XLI

Injectable Preparation

One thousand grams of 4-diethylamino-6phenylpyrimidine hydrochloride are intimately mixed and ground with 2500 grams of sodium ascorbate. The ground dry mixture is placed in vials and sterilized with ethylene oxide after which the vials are sterilely stopped. For intravenous administration, sufficient water is added to the materials in the vials to form a solution containing 10 mg. of active ingredient per milliliter of injectable solution.

EXAMPLE XLII

Suspension

A suspension of 4-diethylamino-6-(m-propionylaminophenyl)pyrimidine is prepared with the following composition:

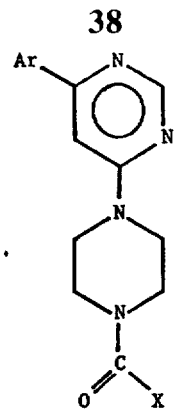

| Ar | X | Ar | X |
|---|---|---|---|
| $C_6H_5$ | $CH_3$ | 4-$FC_6H_4$ | $OCH(CH_3)_2$ |
| $C_6H_5$ | $CH(CH_3)_2$ | 4-$FC_6H_4$ | $CH_3$ |
| $C_6H_5$ | $OCH_3$ | 4-$FC_6H_4$ | 2-furyl |
| 4-$ClC_6H_4$ | $C_2H_5$ | 3-$BrC_6H_4$ | 2-furyl |
| 4-$ClC_6H_4$ | $OC_2H_5$ | 3-$BrC_6H_4$ | $C_2H_5$ |
| 4-$ClC_6H_4$ | $C_6H_5$ | 3-$BrC_6H_4$ | $OCH_2C(CH_3)=CH_2$ |
| 4-$OCH_3C_6H_4$ | $OCH_2C_6H_5$ | 3-$N(CH_3)_2C_6H_4$ | $OCH_2C(CH_3)=CH_2$ |
| 4-$OCH_3C_6H_4$ | $CH_3$ | 3-$N(CH_3)_2C_6H_4$ | 2-furyl |
| 4-$OCH_3C_6H_4$ | 2-furyl | 3-$N(CH_3)_2C_6H_4$ | 2-thienyl |
| 3-$ClC_6H_4$ | $OCH_2C(CH_3)=CH_2$ | 3-$NHCOCH_3C_6H_4$ | $OC_2H_5$ |
| 3-$ClC_6H_4$ | $OCH_2C(CH_3)_3$ | 3-$NHCOCH_3C_6H_4$ | $C_2H_5$ |
| 3-$ClC_6H_4$ | 2-thienyl | 3-$NHCOCH_3C_6H_4$ | 1-piperidyl |
| 4-$CH_3C_6H_4$ | 2-thienyl | 3-$NHCOCH_3C_6H_4$ | $OCH_2C_6H_5$ |
| 4-$CH_3C_6H_4$ | 1-piperidyl | | |
| 4-$CH_3C_6H_4$ | $N(CH_3)_2$ | | |

| | |
|---|---|
| Effective ingredient | 25.00 g. |
| 70% Aqueous sorbitol | 741.29 g. |
| Glycerine, U.S.P. | 185.35 g. |
| Gum acacia (10% solution) | 100.00 ml. |
| Polyvinylpyrrolidone | 0.50 g. |
| Distilled water | Sufficient to make 1 liter |

To this suspension, various sweeteners and flavorants are added to improve the palatability of the suspension. The suspension contains approximately 25 mg. of effective agent per milliliter.

EXAMPLE XLIII

Solution

A solution of 4-diethylamino-6-(p-methoxyphenyl)-pyrimidine hydrochloride is prepared with the following composition:

| | |
|---|---|
| Effective ingredient | 30.22 grams |
| Magnesium chloride hexahydrate | 12.36 grams |
| Monoathanolamine | 8.85 ml. |
| Propylene glycol | 376.00 grams |
| Water, distilled | 94.00 ml. |

The resultant solution has a concentration of effective ingredient of 50 mg./ml. and is suitable for parenteral and especially for intramuscular administration.

EXAMPLE XLIV

Starting with the appropriately substituted 4-chloro-6-arylpyrimidine and requisite piperazine and repeating the procedure of Example I-D, the following analogs are prepared in good yields:

EXAMPLE XLV

In Vitro Inhibition of Platelet Aggregation

The ability of the compounds of the present invention to inhibit platelet aggregation in vitro is measured according to the method of Born, et al., J. Physiol., 168, 178 (1963) and comprises the following procedure:

Anesthetized male rabbits are bled from a carotid artery into plastic centrifuge tubes containing 0.1 volume 3% sodium citrate. Platelet-rich plasma is separated by centrifugation at 100 G for 10 minutes at 20° C. Plasma from 3 animals is pooled; 5 ml. samples are placed into clear plastic curvettes and stirred at 1000 rpm, followed by the addition of compounds of the present invention at levels of $6 \times 10^{-4}$, $10^{-5}$ and $10^{-6}$ moles/liter. After 10 minutes of incubation with the platelet-rich plasma at room temperature, collagen, a protein known to cause platelet aggregation, is added (0.27 ml. collagen/4 ml. plasma) and changes in the optical density are followed with a Spectronic 20 colorimeter attached to a Houston Instrument TY Recorder. Platelet aggregation is indicated by a decrease in optical density. The relative potency of the compounds of the present invention are thus rated on their ability to inhibit (percent) collagen induced platelet aggregation.

The following compounds were evaluated:

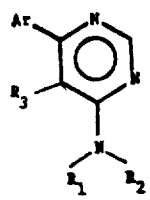

| Ar | $R_1$ | $R_2$ | $R_3$ | % Inhibition Concentration mol./l. $6 \times 10^{-4}$ | $6 \times 10^{-5}$ | $6 \times 10^{-6}$ |
|---|---|---|---|---|---|---|
| $C_6H_5$ | H | H | H | 75 | 65 | — |
| $C_6H_5$ | $CH_3$ | H | H | 99 | 66 | — |
| $C_6H_5$ | $C_2H_5$ | H | H | 99 | 91 | 99 |
| $C_6H_5$ | $i$-$C_3H_7$ | H | H | — | 88 | 29 |
| $C_6H_5$ | $n$-$C_4H_9$ | H | H | — | 42 | 30 |
| $C_6H_5$ | $i$-$C_4H_9$ | H | H | — | 82 | 17 |
| $C_6H_5$ | $CF_3CH_2$ | H | H | — | 83 | 32 |
| $C_6H_5$ | 3-picolyl | H | H | 98 | 31 | 12 |
| $C_6H_5$ | $(CH_3)_2N(CH_2)_2$ | H | H | 99 | 30 | — |
| $C_6H_5$ | $CH_3$ | $CH_3$ | H | 99 | 55 | — |
| $C_6H_5$ | $HO(CH_2)_2$— | $CH_3$ | H | 99 | 99 | 28 |
| $C_6H_5$ | 3-picolyl | $CH_3$ | H | 99 | 17 | — |
| $C_6H_5$ | $n$-$C_3H_7$ | $CH_3$ | H | — | 47 | 39 |
| $C_6H_5$ | $C_2H_5$ | $C_2H_5$ | H | 99 | — | 99 |
| $C_6H_5$ | $HO(CH_2)_2$— | $C_2H_5$ | H | 99 | 97 | 35 |
| $C_6H_5$ | $n$-$C_3H_7$ | $C_2H_5$ | H | 99 | 86 | 79 |
| $C_6H_5$ | $CF_3CH_2$ | $C_2H_5$ | H | 65 | 39 | 34 |
| $C_6H_5$ | $n$-$C_3H_7$ | $n$-$C_3H_7$ | H | 83 | 49 | 41 |
| $C_6H_5$ | $n$-$C_4H_9$ | $n$-$C_4H_9$ | H | — | 56 | 35 |
| $C_6H_5$ | $i$-$C_4H_9$ | $i$-$C_4H_9$ | H | 35 | 24 | 10 |
| $C_6H_5$ | $HO(CH_2)_2$— | $HO(CH_2)_2$— | H | 84 | 27 | — |
| $C_6H_5$ | —$(CH_2)_4$— | | H | 98 | 70 | 6 |
| $C_6H_5$ | $C_2H_5$ | — | $C_2H_5$ | — | — | 80 |
| $C_6H_5$ | $n$-$C_3H_7$ | $n$-$C_3H_7$ | $CH_3$ | — | — | 11 |
| $C_6H_5$ | $CH_3$ | $CH_3$ | $C_2H_5$ | — | — | 50 |
| $C_6H_5$ | $C_2H_5$ | $C_2H_5$ | $C_2H_5$ | — | — | 48 |
| $C_6H_5$ | $n$-$C_3H_7$ | $n$-$C_3H_7$ | $C_2H_5$ | — | — | 5 |
| $C_6H_5$ | $CH_3$ | $CH_3$ | $n$-$C_3H_7$ | — | — | 40 |
| $C_6H_5$ | —$(CH_2)_5$— | | H | 94 | 61 | 60 |
| $C_6H_5$ | —$(CH_2)_6$— | | H | 99 | 83 | 29 |
| $C_6H_5$ | —$(CH_2)_2O(CH_2)_2$— | | H | 94 | 75 | 37 |
| $C_6H_5$ | —$(CH_2)_2N(CH_3)(CH_2)_2$— | | H | 99 | 99 | 59 |
| 3-$CF_3C_6H_4$ | $n$-$C_3H_7$ | $n$-$C_3H_7$ | H | 99 | 50 | — |
| 4-$ClC_6H_4$ | $CF_3CH_2$ | H | H | 86 | 18 | — |
| 4-$ClC_6H_4$ | $CH_3$ | $CH_3$ | H | 99 | 58 | 7 |
| 4-$ClC_6H_4$ | $C_2H_5$ | $C_2H_5$ | H | — | 73 | 32 |
| 4-$ClC_6H_4$ | $C_2H_5$ | $HO(CH_2)_2$— | H | — | 57 | 18 |
| 4-$ClC_6H_4$ | $n$-$C_3H_7$ | $n$-$C_3H_7$ | H | 84 | 70 | — |
| 4-$ClC_6H_4$ | —$(CH_2)_4$— | | H | 99 | 21 | — |
| 4-$ClC_6H_4$ | —$(CH_2)_2N(CH_3)(CH_2)_2$— | | H | 99 | 65 | 2 |
| 4-$CH_3OC_6H_4$ | H | H | H | 72 | 24 | 3 |
| 4-$CH_3OC_6H_4$ | H | $CH_3$ | H | 76 | 13 | — |
| 4-$CH_3OC_6H_4$ | H | $C_2H_5$ | H | 92 | 64 | 24 |
| 4-$CH_3OC_6H_4$ | H | $i$-$C_4H_9$ | H | 76 | 54 | 24 |
| 4-$CH_3OC_6H_4$ | $CH_3$ | $CH_3$ | H | 89 | 88 | 48 |
| 4-$CH_3OC_6H_4$ | $C_2H_5$ | $C_2H_5$ | H | — | 86 | 42 |
| 4-$CH_3OC_6H_4$ | $C_2H_5$ | $HO(CH_2)_2$— | H | 90 | 71 | 55 |
| 4-$CH_3OC_6H_4$ | $n$-$C_3H_7$ | $n$-$C_3H_7$ | H | 91 | 77 | 64 |
| 4-$CH_3OC_6H_4$ | $CH_2=CHCH_2$ | $CH_2=CHCH_2$ | H | 90 | — | 55 |
| 4-$CH_3OC_6H_4$ | —$(CH_2)_4$— | | H | 92 | 92 | 39 |
| 4-$CH_3OC_6H_4$ | —$(CH_2)_2N(CH_3)(CH_2)_2$— | | H | 85 | 55 | 14 |
| 4-$CH_3OC_6H_4$ | $C_2H_5$ | $C_2H_5$ | $C_2H_5$ | — | — | 42 |
| $C_6H_5$ | $C_2H_5$ | $C_2H_5$ | $n$-$C_3H_7$ | — | — | 55 |
| $C_6H_5$ | $C_2H_5$ | $C_2H_5$ | $i$-$C_3H_7$ | — | — | 63 |
| 2-furyl | $C_2H_5$ | $C_2H_5$ | $C_2H_5$ | — | 30 | — |
| 3-$NO_2C_6H_4$ | $C_2H_5$ | $C_2H_5$ | H | 99 | 93 | 25 |
| 3-$NO_2C_6H_4$ | —$(CH_2)_4$— | | H | 94 | 25 | — |
| 3-$NH_2C_6H_4$ | $C_2H_5$ | $C_2H_5$ | H | — | 67 | 41 |
| 3-$NH_2C_6H_4$ | $n$-$C_3H_7$ | $n$-$C_3H_7$ | H | 95 | 97 | 32 |
| 3-$NH_2C_6H_4$ | —$(CH_2)_4$— | | H | 11 | — | — |
| 3-$CH_3CONHC_6H_4$ | $CH_3$ | $CH_3$ | H | 93 | 13 | — |
| 3-$CH_3CONHC_6H_4$ | $C_2H_5$ | $C_2H_5$ | H | — | 16 | 14 |
| 3-$CH_3CONHC_6H_4$ | $n$-$C_3H_7$ | $n$-$C_3H_7$ | H | 88 | 29 | 22 |
| 3-$CH_3CONHC_6H_4$ | $n$-$C_4H_9$ | $n$-$C_4H_9$ | H | 15 | — | — |
| 3-$CH_3CONHC_6H_4$ | —$(CH_2)_4$— | | H | 94 | 30 | — |
| 3-$C_2H_5CONHC_6H_4$ | $C_2H_5$ | $C_2H_5$ | H | 99 | 82 | 13 |
| 3-$C_3H_7CONHC_6H_4$ | $C_2H_5$ | $C_2H_5$ | H | 36 | 8 | — |
| 3-$CH_3SO_2NHC_6H_4$ | $C_2H_5$ | $C_2H_5$ | H | 95 | 21 | 9 |
| 3-$CH_3SO_2NHC_6H_4$ | $n$-$C_3H_7$ | $n$-$C_3H_7$ | H | 94 | 3 | — |
| 3-$CH_3O_2CNHC_6H_4$ | $C_2H_5$ | $C_2H_5$ | H | 95 | 11 | — |
| 3-$CH_3NHCONHC_6H_4$ | $C_2H_5$ | $C_2H_5$ | H | 23 | — | — |
| 3-$CH_3NHCSNHC_6H_4$ | $C_2H_5$ | $C_2H_5$ | H | 4.9 | — | — |
| 2-thienyl | $CH_3$ | $CH_3$ | H | 94 | 82 | 59 |
| 2-thienyl | $C_2H_5$ | H | H | 99 | 75 | 35 |
| 2-thienyl | $C_2H_5$ | $C_2H_5$ | H | 94 | — | 75 |
| 2-thienyl | $n$-$C_3H_7$ | $n$-$C_3H_7$ | H | 60 | 60 | 66 |
| 2-thienyl | $CF_3CH_2$ | H | H | — | 81 | 14 |
| 2-thienyl | $CH_2=CHCH_2$ | $CH_2=CHCH_2$ | H | — | 50 | 40 |
| 2-thienyl | H | H | H | 91 | 9 | — |
| 2-thienyl | $CF_3CH_2$ | $C_2H_5$ | H | 75 | 65 | 58 |
| 3-$(CH_3)_2NC_6H_4$ | $C_2H_5$ | $C_2H_5$ | H | 89 | 95 | 85 |

EXAMPLE XLVI

In Vivo Inhibition of Platelet Aggregation

The capacity of the compounds of the present invention to inhibit platelet aggregation in a modified in vivo test is measured by the following procedure:

Unanesthetized fasted adult mongrel dogs of either sex are dosed orally (P.O.) or intravenously (I.V.) with the particular test compound. Blood samples are taken at hourly intervals and placed in plastic centrifuge tubes containing 0.1 volume 3% sodium citrate. Platelet-rich plasma is separated by centrifugation at 100 G for 10 minutes at 20° C. and treated with a collagen suspension in saline. The effect of two different levels of collagen concentration are examined; the first is a 1:20 dilution, i.e. 1 ml. of collagen suspension per 20 ml. of platelet-rich plasma (high dose), and the second, a 1:40–50 dilution (low dose). Changes in optical density are then followed with a Spectronic 20 colorimeter attached to a Houston Instrument TY Recorder. Platelet aggregation is indicated by a decrease in optical density. The degree of inhibition of collagen induced aggregation is reported as complete (95–100%), partial (15–95%) and none (0–15%). Measurements are carried out on the hourly samples, allowing for the determination of a duration of the initial effect.

Employing the above described procedure the following compounds were tested:

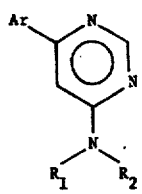

$Ar = C_6H_5$; $R_1 = C_2H_5$; $R_2 = HO(CH_2)_2$:

| Dose, mg./kg. | Route | Inhibition to Collagen High | Low | Duration |
|---|---|---|---|---|
| 10 | I.V. | Complete | Complete | 3 hrs. |
| 25 | P.O. | Complete | Complete | 2 hrs. |

$Ar = C_6H_5$; $R_1 = H$; $R_2 = CH_2CF_3$:

| | | | | |
|---|---|---|---|---|
| 25 | P.O. | Partial | — | 3 hrs. |
| 35 | P.O. | Complete | Complete | 4 hrs. |
| 10 | I.V. | Complete | — | 3 hrs. |

$Ar = C_6H_5$; $R_1, R_2 = C_2H_5$:

| | | | | |
|---|---|---|---|---|
| 25 | P.O | Complete | Complete | 5 hrs. |

$Ar = 4\text{-}CH_3OC_6H_4$; $R_1, R_2 = C_2H_5$:

| | | | | |
|---|---|---|---|---|
| 10 | I.V. | None | None | — |
| 40 | P.O. | — | Complete | 4 hrs. |
| 40 | P.O. | Partial | — | 1 hr. |

EXAMPLE XLVII

Bronchodilator Activity

Conscious female guinea pigs, which have been fasted for 12 hours, receive oral or parenteral dosages of the compound which is to be tested for effectiveness. Control animals receive doses of saline solution which do not contain the compound which is under test. Subsequent to this administration, each animal is challenged with histamine aerosol.

The challenge procedure consists of spraying a 0.4 percent aqueous solution of histamine, at a pressure of 5 lb./in.$^2$ into an 8 × 8 × 12 inch plastic container for one minute. Immediately after the container is subjected to the histamine spray the animal is placed within it. At the end of one minute of exposure, the respiratory status, which is a reflection of bronchoconstriction, is evaluated. Evaluation levels are designated and scored as normal breathing (0), slight deepened breathing (1), labored breathing (2), severely labored breathing and ataxis (3) and unconsciousness (4). Each group of animals contains 8 to 10 individual and a control group containing the same approximate number is used. The scores for the control group and the group which has been treated with the compound under test are compared and the difference is expressed as percent protection.

The dose, which is given orally, is 60 mg./kg. and the animals are challenged with histamine 60 minutes later. The standard compound used is theophylline, which gives 25 percent protection when a dose of 60 mg./kg. is administered orally and the animal is challenged one hour later. When the compounds listed below are administered according to this procedure and the animals are challenged accordingly, the following percent protection is observed.

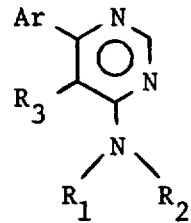

| Ar | $R_1$ | $R_2$ | $R_3$ | % Protection |
|---|---|---|---|---|
| 3-NO$_2$C$_6$H$_4$ | C$_2$H$_5$ | C$_2$H$_5$ | H | 20 |
| 3-CH$_3$CONHC$_6$H$_4$ | C$_2$H$_5$ | C$_2$H$_5$ | H | 40 |
| 3-CH$_3$CONHC$_6$H$_4$ | n-C$_3$H$_7$ | n-C$_3$H$_7$ | H | 30 |
| 3-C$_2$H$_5$CONHC$_6$H$_4$ | C$_2$H$_5$ | C$_2$H$_5$ | H | 30 |
| 3-(CH$_3$)$_2$CHCONHC$_6$H$_4$ | C$_2$H$_5$ | C$_2$H$_5$ | H | 22 |
| 4-CH$_3$CONHC$_6$H$_4$ | C$_2$H$_5$ | C$_2$H$_5$ | H | 56 |
| 3-CH$_3$SO$_2$NHC$_6$H$_4$ | C$_2$H$_5$ | C$_2$H$_5$ | H | 19 |
| 2-furyl | C$_2$H$_5$ | C$_2$H$_5$ | H | 15 |
| 2-naphthyl | C$_2$H$_5$ | C$_2$H$_5$ | C$_2$H$_5$ | 47 |
| 3-CH$_3$CONHC$_6$H$_4$ | C$_2$H$_5$ | C$_2$H$_5$ | CH$_3$ | 43 |
| 3-CH$_3$CONHC$_6$H$_4$ | n-C$_3$H$_7$ | n-C$_3$H$_7$ | CH$_3$ | 17 |
| 3-CH$_3$CONHC$_6$H$_4$ | C$_2$H$_5$ | C$_2$H$_5$ | C$_2$H$_5$ | 35 |
| 3-CH$_3$CONHC$_6$H$_4$ | C$_2$H$_5$ | C$_2$H$_5$ | n-C$_3$H$_7$ | 29 |
| 3-CH$_3$CONHC$_6$H$_4$ | CH$_3$ | CH$_3$ | C$_2$H$_5$ | 10 | and

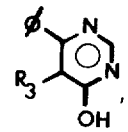

| | | | | |
|---|---|---|---|---|
| | | | H | 12 |
| | | | CH$_3$ | 22 |
| | | | C$_2$H$_5$ | 62 |
| | | | n-C$_3$H$_7$ | 25 |
| | | | i-C$_3$H$_7$ | 16 |

EXAMPLE XLVIII

In vitro Inhibition of Platelet Aggregation in Human Plasma

The procedure of Example XLV is repeated except that platelet-rich plasma from nine human volunteers is employed in place of rabbit plasma. 4-(Diethylamino)-6-phenylpyrimidine hydrochloride provides the following inhibition (%) of collagen induced platelet aggregation at the indicated concentrations:

| Mean % Inhibition | Concentration mol./l. |
|---|---|
| 15 | $6 \times 10^{-7}$ |
| 52 | $6 \times 10^{-6}$ |
| 59 | $6 \times 10^{-5}$ | 
| 73 | $6 \times 10^{-4}$ |

PREPARATION A

Ethyl β-amino-β-arylacrylates

Employing the procedure of Example IA, which is essentialy that taught by Lukes, et al., Chem. Listy, 50, 278 (1956), (C.A. 50, 7796d), the following arylacrylates not previously reported in the literature are synthesized:

$$Ar-\underset{NH_2}{\overset{|}{C}}=CR_3-CO_2C_2H_5$$

| Ar | $R_3$ | Ar | $R_3$ |
|---|---|---|---|
| o-ClC$_6$H$_4$ | H, CH$_3$ and C$_2$H$_5$ | o-CH$_3$OC$_6$H$_4$ | H, CH$_3$ and C$_2$H$_5$ |
| m-ClC$_6$H$_4$ | H, CH$_3$ and C$_2$H$_5$ | m-CH$_3$OC$_6$H$_4$ | H, CH$_3$ and C$_2$H$_5$ |
| p-ClC$_6$H$_4$ | H, CH$_3$ and C$_2$H$_5$ | p-CH$_3$OC$_6$H$_4$ | H, C$_2$H$_5$ and n-C$_3$H$_7$ |
| m-CF$_3$C$_6$H$_4$ | H, CH$_3$ and C$_2$H$_5$ | o-CH$_3$C$_6$H$_4$ | H, CH$_3$ and C$_2$H$_5$ |
| p-CF$_3$C$_6$H$_4$ | H, CH$_3$ and i-C$_3$H$_7$ | m-CH$_3$C$_6$H$_4$ | H and n-C$_3$H$_7$ |
| o-BrC$_6$H$_4$ | H, CH$_3$ and C$_2$H$_5$ | p-CH$_3$C$_6$H$_4$ | H, CH$_3$ and C$_2$H$_5$ |
| m-BrC$_6$H$_4$ | H, CH$_3$ and n-C$_3$H$_7$ | 2-thienyl | H, CH$_3$ and C$_2$H$_5$ |
| p-BrC$_6$H$_4$ | H and C$_2$H$_5$ | 2-benzothienyl | H and CH$_3$ |
| o-FC$_6$H$_4$ | H and C$_2$H$_5$ | 3-benzothienyl | H and C$_2$H$_5$ |
| m-FC$_6$H$_4$ | H and CH$_3$ | 3,4-(CH$_3$O)$_2$C$_6$H$_3$ | H and C$_2$H$_5$ |
| p-FC$_6$H$_4$ | H and CH$_3$ | 3-thienyl | C$_2$H$_5$ and n-C$_3$H$_7$ |

PREPARATION B

4-Hydroxy-6-arylpyrimidines

The following 4-hydroxy-6-arylpyrimidines, previously unreported in the chemical literature, are prepared from the requisite starting materials employing the reaction procedures of Example IB and IIIB.

[Structure: Ar and $R_3$ substituted pyrimidine with OH group]

| Ar | $R_3$ | Ar | $R_3$ |
|---|---|---|---|
| o-ClC$_6$H$_4$ | H | o-CH$_3$OC$_6$H$_4$ | H |
| o-ClC$_6$H$_4$ | CH$_3$ | o-CH$_3$OC$_6$H$_4$ | CH$_3$ |
| o-ClC$_6$H$_4$ | C$_2$H$_5$ | o-CH$_3$OC$_6$H$_4$ | C$_2$H$_5$ |
| m-ClC$_6$H$_4$ | H | m-CH$_3$OC$_6$H$_4$ | H |
| p-ClC$_6$H$_4$ | H | p-CH$_3$OC$_6$H$_4$ | H |
| m-CF$_3$C$_6$H$_4$ | H | p-CH$_3$OC$_6$H$_4$ | C$_2$H$_5$ |
| p-CF$_3$C$_6$H$_4$ | H | p-CH$_3$OC$_6$H$_4$ | n-C$_3$H$_7$ |
| p-CF$_3$C$_6$H$_4$ | CH$_3$ | o-CH$_3$C$_6$H$_4$ | H |
| p-CF$_3$C$_6$H$_4$ | i-C$_3$H$_7$ | o-CH$_3$C$_6$H$_4$ | CH$_3$ |
| o-BrC$_6$H$_4$ | H | o-CH$_3$C$_6$H$_4$ | C$_2$H$_5$ |
| o-BrC$_6$H$_4$ | CH$_3$ | m-CH$_3$C$_6$H$_4$ | H |
| o-BrC$_6$H$_4$ | C$_2$H$_5$ | m-CH$_3$C$_6$H$_4$ | n-C$_3$H$_7$ |
| m-BrC$_6$H$_4$ | H | p-CH$_3$C$_6$H$_4$ | H |
| m-BrC$_6$H$_4$ | CH$_3$ | p-CH$_3$C$_6$H$_4$ | CH$_3$ |
| m-BrC$_6$H$_4$ | n-C$_3$H$_7$ | p-CH$_3$C$_6$H$_4$ | C$_2$H$_5$ |
| p-BrC$_6$H$_4$ | H | 2-thienyl | H |
| p-BrC$_6$H$_4$ | C$_2$H$_5$ | 2-thienyl | CH$_3$ |
| o-FC$_6$H$_4$ | H | 2-thienyl | C$_2$H$_5$ |
| o-FC$_6$H$_4$ | C$_2$H$_5$ | 3-thienyl | C$_2$H$_5$ |
| m-FC$_6$H$_4$ | H | 3-thienyl | C$_2$H$_5$ |
| m-FC$_6$H$_4$ | CH$_3$ | 3-thienyl | n-C$_3$H$_7$ |
| p-FC$_6$H$_4$ | H | 2-benzothienyl | H |
| p-FC$_6$H$_4$ | CH$_3$ | 2-benzothienyl | CH$_3$ |
| 3-benzothienyl | H | m-CH$_3$OC$_6$H$_4$ | H |
| 3-benzothienyl | C$_2$H$_5$ | p-CH$_3$OC$_6$H$_4$ | H |
| 3,4-(CH$_3$O)$_2$C$_6$H$_3$ | H | p-CH$_3$OC$_6$H$_4$ | CH$_3$ |
| o-HO$_2$CC$_6$H$_4$ | H | 2-indolyl | H |
| o-HO$_2$CC$_6$H$_4$ | CH$_3$ | 2-indolyl | CH$_3$ |
| m-HO$_2$CC$_6$H$_4$ | H | 3-indolyl | H |
| p-HO$_2$CC$_6$H$_4$ | H | 3-indolyl | C$_2$H$_5$ |
| p-HO$_2$CC$_6$H$_4$ | CH$_3$ | 2-benzofuryl | H |
| p-HO$_2$CC$_6$H$_4$ | C$_2$H$_5$ | 2-benzofuryl | n-C$_3$H$_7$ |
| o-CNC$_6$H$_4$ | H | 3-benzofuryl | H |
| o-CNC$_6$H$_4$ | CH$_3$ | 3-benzofuryl | i-C$_3$H$_7$ |
| o-CNC$_6$H$_4$ | C$_2$H$_5$ | 3-NO$_2$-2-pyridyl | H |
| p-CNC$_6$H$_4$ | H | 4-NO$_2$-2-pyridyl | H |
| p-CNC$_6$H$_4$ | n-C$_3$H$_7$ | 4-NO$_2$-2-pyridyl | C$_2$H$_5$ |
| C$_6$H$_5$ | n-C$_3$H$_7$ | 5-NO$_2$-2-pyridyl | H |
| C$_6$H$_5$ | i-C$_3$H$_7$ | 5-NO$_2$-2-pyridyl | CH$_3$ |
| 2-furyl | C$_2$H$_5$ | 5-NO$_2$-2-pyridyl | n-C$_3$H$_7$ |
| 3-furyl | CH$_3$ | 4-NO$_2$-3-pyridyl | H |
| 3-furyl | C$_2$H$_5$ | 5-NO$_2$-3-pyridyl | H |
| 1-naphthyl | C$_2$H$_5$ | 6-NO$_2$-3-pyridyl | H |
| 2-naphthyl | C$_2$H$_5$ | 2-NO$_2$-4-pyridyl | H |
|  |  | 3-NO$_2$-4-pyridyl | H |

PREPARATION C

4-Chloro-6-arylpyrimidines

Following the experimental procedures of Examples IC and IIC the following 4-chloro-6-arylpyrimidines, unreported in the literature, are prepared:

[Structure: Ar and $R_3$ substituted pyrimidine with Cl group]

| Ar | $R_3$ | Ar | $R_3$ |
|---|---|---|---|
| o-ClC$_6$H$_4$ | H | o-CH$_3$OC$_6$H$_4$ | H |
| o-ClC$_6$H$_4$ | CH$_3$ | o-CH$_3$OC$_6$H$_4$ | CH$_3$ |
| o-ClC$_6$H$_4$ | C$_2$H$_5$ | o-CH$_3$OC$_6$H$_4$ | C$_2$H$_5$ |
| m-ClC$_6$H$_4$ | H | m-CH$_3$OC$_6$H$_4$ | H |
| p-ClC$_6$H$_4$ | H | p-CH$_3$OC$_6$H$_4$ | H |
| m-CF$_3$C$_6$H$_4$ | H | p-CH$_3$OC$_6$H$_4$ | C$_2$H$_5$ |
| p-CF$_3$C$_6$H$_4$ | H | p-CH$_3$OC$_6$H$_4$ | n-C$_3$H$_7$ |
| p-CF$_3$C$_6$H$_4$ | CH$_3$ | o-CH$_3$C$_6$H$_4$ | H |
| p-CF$_3$C$_6$H$_4$ | i-C$_3$H$_7$ | o-CH$_3$C$_6$H$_4$ | CH$_3$ |
| o-BrC$_6$H$_4$ | H | o-CH$_3$C$_6$H$_4$ | C$_2$H$_5$ |
| o-BrC$_6$H$_4$ | CH$_3$ | m-CH$_3$C$_6$H$_4$ | H |
| o-BrC$_6$H$_4$ | C$_2$H$_5$ | m-CH$_3$C$_6$H$_4$ | n-C$_3$H$_7$ |
| m-BrC$_6$H$_4$ | H | p-CH$_3$C$_6$H$_4$ | H |
| m-BrC$_6$H$_4$ | CH$_3$ | p-CH$_3$C$_6$H$_4$ | CH$_3$ |

-continued

| Ar | R₃ | Ar | R₃ |
|---|---|---|---|
| m-BrC₆H₄ | n-C₃H₇ | p-CH₃C₆H₄ | C₂H₅ |
| p-BrC₆H₄ | H | 2-thienyl | H |
| p-BrC₆H₄ | C₂H₅ | 2-thienyl | CH₃ |
| o-FC₆H₄ | H | 2-thienyl | C₂H₅ |
| o-FC₆H₄ | C₂H₅ | 3-thienyl | C₂H₅ |
| m-FC₆H₄ | H | 3-thienyl | n-C₃H₇ |
| m-FC₆H₄ | CH₃ | 2-benzothienyl | H |
| p-FC₆H₄ | H | 2-benzothienyl | CH₃ |
| 3-benzothienyl | H | m-CH₃OC₆H₄ | H |
| 3-benzothienyl | C₂H₅ | p-CH₃COC₆H₄ | H |
| 3,4-(CH₃O)₂C₆H₃ | H | p-CH₃COC₆H₄ | CH₃ |
| o-HO₂CC₆H₄ | H | 2-indolyl | H |
| o-HO₂CC₆H₄ | CH₃ | 2-indolyl | CH₃ |
| m-HO₂CC₆H₄ | H | 3-indolyl | H |
| p-HO₂CC₆H₄ | H | 3-indolyl | C₂H₅ |
| p-HO₂CC₆H₄ | CH₃ | 2-benzofuryl | H |
| p-HO₂CC₆H₄ | C₂H₅ | 2-benzofuryl | n-C₃H₇ |
| o-CNC₆H₄ | H | 3-benzofuryl | H |
| o-CNC₆H₄ | CH₃ | 3-benzofuryl | i-C₃H₇ |
| o-CNC₆H₄ | C₂H₅ | 3-NO₂-2-pyridyl | H |
| p-CNC₆H₄ | H | 4-NO₂-2-pyridyl | H |
| p-CNC₆H₄ | n-C₃H₇ | 4-NO₂-2-pyridyl | C₂H₅ |

| | | | |
|---|---|---|---|
| C₆H₅ | n-C₃H₇ | 5-NO₂-2-pyridyl | H |
| C₆H₅ | i-C₃H₇ | 5-NO₂-2-pyridyl | CH₃ |
| 2-furyl | C₂H₅ | 5-NO₂-2-pyridyl | n-C₃H₇ |
| 3-furyl | CH₃ | 4-NO₂-3-pyridyl | H |
| 3-furyl | C₂H₅ | 5-NO₂-3-pyridyl | H |
| 1-naphthyl | C₂H₅ | 6-NO₂-3-pyridyl | H |
| 2-naphthyl | C₂H₅ | 2-NO₂-4-pyridyl | H |
| | | 3-NO₂-4-pyridyl | H |

PREPARATION D

Ethyl Aroylacetates a. ethyl 1-naphthoylacetate.

To 3.62 g. of sodium dissolved in 125 ml. of absolute ethanol is added 20.4 g. of ethyl acetoacetate and the mixture cooled to 0°C. while 15.35 g. of naphthoyl chloride in 75 ml. of benzene is added with stirring. After 30 minutes, solutions of 3.62 g. of sodium in 125 ml. of ethanol and 15.35 g. of naphthoyl chloride in 75 ml. of benzene are added simultaneously to the reaction mixture. The precipitate is filtered, taken up in several volumes of water and treated with a 10% cupric acetate solution. The precipitated copper complex (23 g.) is decomposed with 20% sulfuric acid to provide 25.5 g. of ethyl α-(1-naphthoyl)acetoacetate which in turn, on treatment with 5% ammonium hydroxide provides the desired product.

The following ethyl aroylacetates not previously reported in the literature are synthesized by the aforedescribed procedure, which is essentially that taught by Libermann, et al., Bull. soc. chim. France, 486 (1950), by techniques outlined by Hauser, et al., "Organic Reactions," John Wiley & Sons, Inc., New York, Volume I, Chapter 9, page 266, or by the method of Hope, et al., J. Chem. Soc. 95, 2045 (1909):

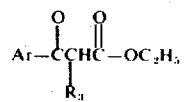

| Ar | R₃ | Ar | R₃ |
|---|---|---|---|
| o-HO₂CC₆H₄ | H and CH₃ | 2-indolyl | H and CH₃ |
| m-HO₂CC₆H₄ | H | 3-indolyl | H and C₂H₅ |
| p-HO₂CC₆H₄ | H, CH₃ and C₂H₅ | 2-benzofuryl | H and n-C₃H₇ |
| o-CNC₆H₄ | H, CH₃ and C₂H₅ | 3-benzofuryl | H and i-C₃H₇ |
| p-CNC₆H₄ | H, n-C₃H₇ | 3-NO₂-2-pyridyl | H |
| C₆H₅ | n- and i-C₃H₇ | 4-NO₂-2-pyridyl | H and C₂H₅ |
| 2-furyl | C₂H₅ | 5-NO₂-2-pyridyl | H, CH₃ and n-C₃H₇ |
| 3-furyl | CH₃ and C₂H₅ | 5- and 6-NO₂-3-pyridyl | H |
| 1- and 2-naphthyl | C₂H₅ | 2- and 3-NO₂-4-pyridyl | H |
| m-CH₃COC₆H₄ | H | | |
| p-CH₃COC₆H₄ | H and CH₃ | | |

PREPARATION E

2-Mercapto-4-hydroxy-6-arylpyrimidines

The following 6-aryl-2-thiouracil intermediates, not previously reported in the literature, are prepared by repetition of the procedure of Example IIIA starting with the appropriate reagents:

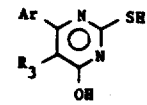

| Ar | R₃ | Ar | R₃ |
|---|---|---|---|
| o-HO₂CC₆H₄ | H and CH₃ | 2-indolyl | H and CH₃ |
| m-HO₂CC₆H₄ | H | 3-indolyl | H and C₂H₅ |
| p-HO₂CC₆H₄ | H, CH₃ and C₂H₅ | 2-benzofuryl | H and n-C₃H₇ |
| o-CNC₆H₄ | H, CH₃ and C₂H₅ | 3-benzofuryl | H and i-C₃H₇ |
| p-CNC₆H₄ | H, n-C₃H₇ | 3-NO₂-2-pyridyl | H |
| C₆H₅ | n- and i-C₃H₇ | 4-NO₂-2-pyridyl | H and C₂H₅ |
| 2-furyl | C₂H₅ | 5-NO₂-2-pyridyl | H, CH₃ and n-C₃H₇ |
| 3-furyl | CH₃ and C₂H₅ | 4-, 5- and 6-NO₂-3-pyridyl | H |
| 1- and 2-naphthyl | C₂H₅ | 2- and 3-NO₂-4-pyridyl | H |
| m-CH₃COC₆H₄ | H | | |
| p-CH₃COC₆H₄ | H and CH₃ | | |

PREPARATION F

Following the procedure of Example IIA and starting with the requisite nitrochlorobenzonitrile the following 2-carbomethoxy-3-aminobenzothiophenes not previously reported in the chemical literature are prepared:

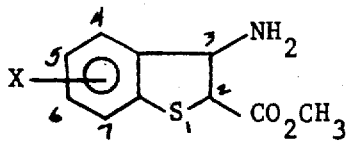

X = 4-NO$_2$ and 6-NO$_2$

PREPARATION G

Starting with 4- and 6-nitro-2-carbomethoxy-3-aminobenzothiophene and employing the procedure of Example IIB the following 4-hydroxybenzothieno-[3,2-d]pyrimidines, not previously reported in the literature, are prepared:

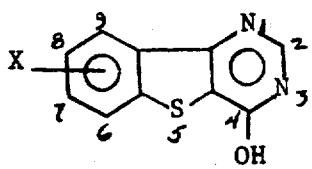

X = 7-NO$_2$ and 9-NO$_2$

PREPARATION H

The procedure of Example IIC is repeated, starting with 7- and 9-nitro-4-hydroxybenzothieno[3,2-d]pyrimidine, to provide the following 4-chlorobenzothieno[3,2-d]pyrimidines, previously unreported in the chemical literature:

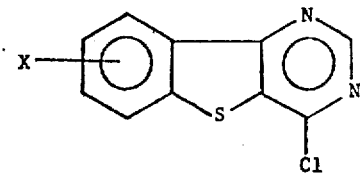

X = 7-NO$_2$ and 9-NO$_2$

PREPARATION I

4-Aminobenzothieno[3,2-d]pyrimidines

Employing the experimental procedures of Example IID, the following previously unreported 4-aminobenzothieno[3,2-d]pyrimidines are synthesized starting from the appropriate intermediates:

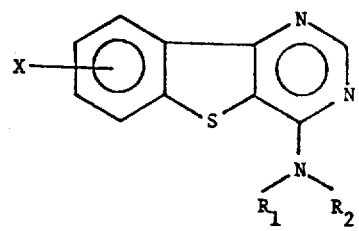

| X | R$_1$ | R$_2$ | X | R$_1$ | R$_2$ |
|---|---|---|---|---|---|
| H | H | 2-pyridylmethyl | 2-NO$_2$ | H | H |
| H | CH$_3$ | 2-pyridylmethyl | 2-NO$_2$ | CH$_3$ | H |
| H | n-C$_3$H$_7$ | 2-pyridylmethyl | 2-NO$_2$ | C$_2$H$_5$ | C$_2$H$_5$ |
| H | H | 3-pyridylmethyl | 2-NO$_2$ | C$_2$H$_5$ | HO(CH$_2$)$_2$— |
| H | CH$_3$ | 3-pyridylmethyl | 2-NO$_2$ | n-C$_3$H$_7$ | C$_2$H$_5$ |
| H | CH$_3$ | 4-pyridylmethyl | 4-NO$_2$ | H | H |
| H | H | 2-H$_2$NSO$_2$C$_6$H$_4$ | 4-NO$_2$ | CH$_3$ | CH$_3$ |
| H | CH$_3$ | 2-H$_2$NSO$_2$C$_6$H$_4$ | 4-NO$_2$ | C$_2$H$_5$ | H |
| H | n-C$_4$H$_9$ | 2-H$_2$NSO$_2$C$_6$H$_4$ | 4-NO$_2$ | C$_2$H$_5$ | HO(CH$_2$)$_2$— |
| H | H | 2-HO$_2$CC$_6$H$_4$ | 4-NO$_2$ | HO(CH$_2$)$_2$— | HO(CH$_2$)$_2$— |
| H | CH$_3$ | 2-HO$_2$CC$_6$H$_4$ | 4-NO$_2$ | n-C$_3$H$_7$ | n-C$_3$H$_7$ |
| H | i-C$_3$H$_7$ | 2-HO$_2$CC$_6$H$_4$ | | | |

What is claimed is:

1. The method of relaxing smooth muscle in a mammal which comprises administering to said mammal an effective amount of a compound of the formula:

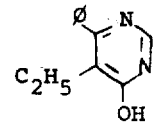

or a pharmaceutically acceptable salt thereof.

* * * * *